US008124344B2

(12) United States Patent
Abe et al.

(10) Patent No.: US 8,124,344 B2
(45) Date of Patent: Feb. 28, 2012

(54) METHOD OF DETERMINING AN AMOUNT OF FATTY ACID CONTENTS IN BOVINE INTRAMUSCULAR FAT ON THE BASIS OF GENOTYPE OF FATTY ACID SYNTHASE GENE AND METHOD OF DETERMINING GOODNESS OF EATING QUALITY OF BEEF ON THE BASIS OF THE RESULTS THEREOF

(75) Inventors: Tsuyoshi Abe, Nishigo-mura (JP); Junichi Saburi, Nishigo-mura (JP); Eiji Kobayashi, Nishigo-mura (JP); Hiroaki Nakajima, Mogami-machi (JP); Noriaki Shoji, Shinjo (JP)

(73) Assignees: National Livestock Breeding Center (NLBC) Incorporated Administrative Agency, Fukushima (JP); Yamagata Prefecture, Yamagata (JP)

( * ) Notice: Subject to any disclaimer, the term of this patent is extended or adjusted under 35 U.S.C. 154(b) by 400 days.

(21) Appl. No.: 12/302,960

(22) PCT Filed: Sep. 4, 2007

(86) PCT No.: PCT/JP2007/067186

§ 371 (c)(1), (2), (4) Date: Dec. 1, 2008

(87) PCT Pub. No.: WO2008/029789

PCT Pub. Date: Mar. 13, 2008

(65) Prior Publication Data

US 2009/0305268 A1 Dec. 10, 2009

(30) Foreign Application Priority Data

Sep. 7, 2006 (JP) ................................ 2006-242487

(51) Int. Cl.
*C12Q 1/68* (2006.01)
*C12P 19/34* (2006.01)

(52) U.S. Cl. ..................... 435/6.11; 435/6.12; 435/6.18

(58) Field of Classification Search ........................ None
See application file for complete search history.

(56) References Cited

U.S. PATENT DOCUMENTS 6,849,401 B1 * 2/2005 Andersson et al. ............... 435/6

OTHER PUBLICATIONS

Roy et al. Animal Genetics, 37, 215-218; plus supplemental table 1, one page.*
Roy et al. 2006. Animal Genetics, 37, 215-218.*
Supplemental Table 2, from Roy et al. 2006, one page.*
Webcutter 2.0 (1997, www.firstmarket.com/cutter/cut2.html <http://www.firstmarket.com/cutter/cut2.html>, accessed Jan. 22, 2004) ; three pages.*
GenBank Record having accession AF285607; Nov. 24, 2003, eleven pages.*

* cited by examiner

*Primary Examiner* — Juliet Switzer
(74) *Attorney, Agent, or Firm* — Antonelli, Terry, Stout & Kraus, LLP.

(57) ABSTRACT

The present invention has an object to provide a method of determining fatty acid composition in intramuscular fat on the basis of bovine genotype, in particular a method of simply determining an amount of an oleic acid content with a high degree of accuracy, and a method of objectively determining the goodness of eating quality of beef on the basis of the results of the determination. The present invention provides a method of determining an amount of fatty acid content in bovine intramuscular fat on the basis of the genotype of fatty acid synthase determined by determining base <1> and/or base <2> described below, and a method of determining whether cattles are those from which beef with an excellent eating quality is obtained on the basis of the results thereof.

<1> A 16,024th base corresponding to a polymorphic site which is either adenine (A) or guanine (G) in a base sequence represented by SEQ ID NO. 1 of a sequence list.

<2> A 16,039th base corresponding to a polymorphic site which is either thymine (T) or cytosine (C) in the same base sequence.

7 Claims, 1 Drawing Sheet

METHOD OF DETERMINING AN AMOUNT OF FATTY ACID CONTENTS IN BOVINE INTRAMUSCULAR FAT ON THE BASIS OF GENOTYPE OF FATTY ACID SYNTHASE GENE AND METHOD OF DETERMINING GOODNESS OF EATING QUALITY OF BEEF ON THE BASIS OF THE RESULTS THEREOF

TECHNICAL FIELD

The present invention relates to a method of determining whether a cattle or beef has a good eating quality by determination of the amount of, in particular, oleic acid among the fatty acid composition included in intramuscular fat on the basis of the genotype of fatty acid synthase (FASN). In addition, the present invention relates to a method of selecting and breeding a cattle from which beef with an excellent eating quality can be obtained on the basis of the results of the determination. In particular, the present invention provides a technology useful in the fields of livestock industry (such as the raising, reproduction, breeding, and improvement of cattle), the production and processing of beef, and the like.

BACKGROUND ART

Among fatty acids included in bovine intramuscular fat, the most abundant one is mono unsaturated fatty acid with 18 carbon atoms (oleic acid). In particular, the beef of Japanese Black breed has been reported as one containing a significantly high amount of oleic acid compared with that of the foreign breed (see Non-patent Document 1). In general, it is said that the beef of Japanese Black breed has an excellent Japanese-preferred eating quality compared with that of the foreign breed. As one of its factors, it may be due to rich oleic acid content in Japanese Black cattle beef in comparison with that of the foreign breed (see Non-patent Document 2).

In order to determine beef fatty acid composition, including oleic acid, large experimental arrangement such as a draft is required, and technical skills are also indispensable for obtaining correct data. Further, there are many other problems such that: it is difficult to process a lot of samples at a time because it takes a long time for the determination; and a large amount of an organic solvent is used in a stage of fatty acid extraction or the like, so the harmful effects of the organic solvent on the health of a person who carries out such a determination cannot be ignored.

On the other hand, currently, the breeding of the beef cattle in Japan is carried out on the basis of the carcass grade determined by the Japan Meat Grading Association.

However, as described above, complicated physiochemical analyses must be required for determining the feature of the fatty acid composition or the like that is associated with the eating-quality of beef. Thus, unlike the carcass grade, the data cannot be easily obtained. Therefore, the feature has not been considered as target traits for improvement till now. As far as such a situation persists, it is probable that the chance of adopting the above feature as the target traits for improvement is low in the future.

Therefore, it has been demanded to develop a method of determining the fatty acid composition of beef on the basis of a genetic base sequence, which can be carried out by a simple device without much need of technical skill.

Heretofore, a technology for evaluating the eating quality of beef by determining the melting point of fat and the unsaturated degree of fatty acid in beef using the genotype of stearoyl-CoA desaturase (SCD) has been already patented (Patent Document 1).

The determination of the eating quality of beef using the SCD gene, which is described in Patent Document 1, is carried out on the basis of the relationship between the eating quality and the melting point of fat in the beef and the relationship between the eating quality and the unsaturated degree of the fatty acid in the beef. In this case, the unsaturated degree of the fatty acid composition is calculated from the ratio of the total content of saturated fatty acids to the total content of mono unsaturated fatty acids in the fatty acids of beef, so it is impossible to obtain the amount of fatty acid separately by every kind thereof.

Fatty acid synthase (FASN) gene is known as an enzyme for fatty acid synthesis in the bovine muscle. The enzyme is one of the enzymes responsible for in vivo fatty acid synthesis. The entire gene sequence from the cattle (*Bos taurus*) and the amino acid sequence estimated therefrom are described in Non-patent Document 3 listed below.

However, any method of determining fatty acid composition on the basis of the genotype of fatty acid synthase has not been known.

Non-patent Document 1: May S. G. et al., Comparison of sensory characteristics and fatty acid composition between Wagyu crossbred and Angus steers, Meat Science 35, 289-298 (1993)

Non-patent Document 2: Matsubara et al., Quality of and Consumer Preference for Marketing Beef, Bull. Hyogo Pre. Agri. Inst. (Animal Husbandry) 34, 10-15 (1998)

Non-patent Document 3: DDBJ/EMBL/GenBank databases: Accession Number AF285607

Patent Document 1: JP 2004-261014 A

DISCLOSURE OF THE INVENTION

Problems to be Solved by the Invention

As described above, the fatty acid composition of bovine intramuscular fat is associated with the eating quality of beef. In particular, the beef with a high oleic acid content is supposed to be excellent in eating quality. If the amount of the oleic acid content can be determined on the basis of the base sequence of the specific bovine gene, the eating quality of the beef will be simply examined. Further, by using the information for breeding and selection, it will be possible to improve the eating quality of beef, which has been almost impossible.

The present invention has been made in consideration of the above circumstances and the object thereof is to provide a method of determining fatty acid composition in intramuscular fat on the basis of the genotype of cattle, in particular a method of simply determining the amount of the oleic acid content with a high degree of accuracy, and to provide a method of determining objectively the eating quality of beef on the basis of the result of the above determination.

Means for Solving the Problems

In consideration of the above problems, the inventors of the present invention have particularly focused on the above fatty acid synthase gene and intensively studied the relationship between the gene and the fatty acid composition in bovine intramuscular fat, particularly the amount of the oleic acid content. As a result, the inventors have finally completed the present invention by finding out the following: (1) single nucleotide polymorphisms (SNPs) are present at two positions of the above gene; (2) the SNPs are very proximal to each other at an interval of only 14 bases and two haplotypes are present; (3) there is a significant difference between two haplotypes with respect to the content of oleic acid in bovine intramuscular fat; and the like.

In the determination of the eating quality of beef by making use of the SCD gene as described in Patent Document 1, it is impossible to obtain the amount of fatty acid separately by every kind thereof as described above.

In contrast, the method of using the genotype of FASN gene of the present invention can determine not only the unsaturation degree of the fatty acid in beef but also the amount of each fatty acid. In other words, for example, it is possible to determine the ratio of the content of mono unsaturated fatty acid with 18 carbon atoms, such as oleic acid, which is suggested to be associated with the eating quality of beef. In addition, it is possible to determine the ratio of the content of each of other fatty acids (the respective fatty acids of C14 and C16 including both saturated and unsaturated types thereof).

Among the fatty acids which can be biosynthesized in the bovine body itself, oleic acid has been suggested to have a relationship with the eating quality of beef as described above. However, according to further progress in studies, other fatty acids than oleic acid, which are considered to have an influence on the eating quality of beef, or fatty acids which may be preferable (or unpreferable) to human health, or the like will be possibly elucidated in the future.

The present invention can be more excellent than the invention of Patent Document 1 in the point of capability of determining the amounts of the fatty acids separately in terms of kind.

In other words, the present invention includes those of industrially-applicable methods and materials as follows.

The first aspect of the present invention, according to a first method, is a method of determining an amount of fatty acid content in bovine intramuscular fat on the basis of the genotype of fatty acid synthase defined by a determination of base <1> and/or base <2> described below:

<1> a 16,024th base corresponding to a polymorphic site which is either adenine (A) or guanine (G) shown in a base sequence represented by SEQ ID NO. 1 of a sequence list; and <2> a 16,039th base corresponding to a polymorphic site which is either thymine (T) or cytosine (C) shown in the base sequence represented by SEQ ID NO. 1 of the sequence list.

The second aspect of the present invention, according to a second method, is the method according to the first method, in which the fatty acid includes oleic acid.

The third aspect of the present invention, according to a third method, is the determination method according to the first or second method, including the steps of:

(a) amplifying a gene region containing the base <1> and the base <2> by a gene amplification reaction using as a template genomic DNA or cDNA prepared from a bovine subject; and (b) digesting an amplified fragment obtained in the step (a) with a restriction enzyme, and determining a genotype of fatty acid synthase based on the presence or absence of cleavage.

The fourth aspect of the present invention, according to a fourth method, is the determination method according to the third method, in which the gene amplification reaction in the above step (a) is carried out by a polymerase-chain reaction using a forward primer consisting of a base sequence represented by SEQ ID NO. 3 of the sequence list and a reverse primer consisting of a base sequence represented by SEQ ID NO. 4 of the sequence list and the restriction enzymes used in the step (b) are HhaI and NciI.

The fifth aspect of the present invention, according to a fifth method, is the determination method according to the first method or the second method, in which the determination of the base <1> and/or the base <2> is carried out using a DNA chip.

The sixth aspect of the present invention, according to a sixth method, is the determination method according to the first or second method, in which the determination of the base <1> and/or the base <2> is carried out using a polymerase chain reaction device equipped with a thermal cycler and a fluorescence detector.

The seventh aspect of the present invention, according to a seventh method, is the determination method according to any one of the previously discussed first through sixth methods, in which the cattle is a beef breed.

The eighth aspect of the present invention, according to an eighth method, is the determination method according to any one of the previously discussed first through sixth methods, in which the cattle is a dairy breed which is also available for a beef breed.

The ninth aspect of the present invention is a kit for detecting a genetic polymorphism to be used in the determination method according to any one of the first, second and fifth through eighth methods previously discussed, including a nucleotide probe that specifically binds to a gene region containing the base <1> and/or the base <2> shown in the base sequence represented by SEQ ID NO. 1 of the sequence list.

The tenth aspect of the present invention is a kit for detecting a genetic polymorphism to be used in the determination method according to any one of the previously discussed first through eighth methods, including a primer for specifically amplifying the gene region containing the base <1> and/or the base <2> shown in the base sequence represented by SEQ ID NO. 1 of the sequence list by a gene amplification reaction.

The eleventh aspect of the present invention is a primer for specifically amplifying the gene region containing the base <1> and/or the base <2> by a gene amplification reaction.

The twelfth aspect of the present invention is a nucleotide probe that specifically binds to the gene region containing the base <1> and/or the base <2>.

The thirteenth aspect of the present invention is a method of determining whether a cattle is a cattle from which beef with an excellent eating quality can be obtained on the basis of a result of the determination method according to any one of the previously discussed first through eighth methods.

The fourteenth aspect of the present invention is a method of selecting and breeding a cattle from which beef with an excellent eating quality can be obtained on the basis of a result of the determination method according to any one of the first through eighth methods previously discussed.

Effects of the Invention

According to the present invention, on the basis of the genotype of fatty acid synthase (FASN), it is possible to determine not only the unsaturation degree of the fatty acid in beef but also the amount of each kind of fatty acid. Further, it is possible to provide a method of determining whether a cattle is available for the production of beef with an excellent eating quality on the basis of such a determination, and a method of carrying out the breeding, selective breeding, or the like of the cattle, whereby providing various kinds of usefulness.

Further, the conventional measurement of the fatty acid composition of beef was complicated and required the complicated and the skilled technology. In contrast, according to the present invention, the amount of the content of fatty acid can be determined using only experimental instruments with simple handling without much skills for operation or the like, such as a thermal cycler or an electrophoretic unit. In addition, a lot of samples can be efficiently determined with high accuracy.

Further, there is a need of collecting a sample after slaughtering for determining the fatty acid composition. According to the present invention, however, a DNA sample may be obtained from a living body (for example, through blood-drawing or hair-root-sampling), so the fatty acid composition can be determined without waiting the period to raise cattle which extends over about 30 months.

DESCRIPTION OF SYMBOLS

Figure 1:
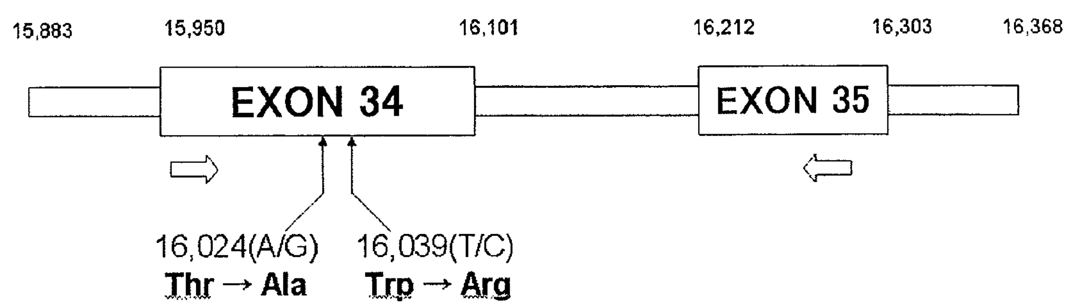
FIG. 1 is a diagram for illustrating single nucleotide polymorphisms (SNPs) at two different positions found on exon 34 of bovine FASN gene and approximate positions of PCR primers for detecting the SNPs.

In FIG. 1, a right pointing white arrow represents a forward primer (SEQ ID NO: 3 of the sequence list) and a left pointing white arrow represents a reverse primer (SEQ ID NO: 4 of the sequence list).

BEST MODE FOR CARRYING OUT THE INVENTION

Hereinafter, specific embodiments of the invention, the technical scope thereof, and the like will be described in detail.

(1) Determination Method of the Present Invention

The invention described in claim 1 provides, as describe above, a method of determining the amount of the content of fatty acid in bovine intramuscular fat on the basis of the genotype of fatty acid synthase.

The term "cattle" used herein means European cattle (*Bos taurus*). The European cattle include Japanese cattle such as Japanese Black, and European domestic cattle such as Holstein, Hereford, Aberdeen Angus, and Limousin breeds. The "cattle" to be provided as targets of the determination (sample) may be any of beef breeds (beef cattle) or dairy breeds (dairy cattle) which is also used for beefs.

In addition, in this specification, the term "fatty acid synthase" (hereinafter, occasionally abbreviated as "FASN") means an enzyme derived from cattle that biosynthesizes fatty acid in vivo. SEQ ID NO. 1 and SEQ ID NO. 2 of the sequence list represents the entire genomic DNA sequence of FASN gene disclosed in Non-patent Document 3 and the amino acid sequence of FASN protein coded by the sequence, respectively. The DNA sequence of SEQ ID NO. 1 and the amino acid sequence of SEQ ID NO. 2 are identical with the sequences disclosed in Non-patent Document 3 but different in notation of single nucleotide polymorphisms (SNPs) as described below.

FIG. 1 schematically represents a genomic-DNA partial sequence containing exon 34 and exon 35 of the above FASN gene. In the figure, large squares represent respective exon regions and small squares represent respective intron regions sandwiching respective exon regions. The respective numerals in the figure represent the number of nucleotide corresponding to each position based on the first nucleotide of the genomic DNA sequence of FASN gene represented by SEQ ID No. 1 of the sequence list.

At the bottom of FIG. 1, there are shown single nucleotide polymorphisms (SNPs) with the substitution of two amino acids found on the FASN gene (without containing untranslated regions), as a result of detailed research and examination carried out by the inventors of the present invention.

The inventors have paid attention to and circumstantially analyzed the above gene because a gene region related to the fatty acid composition has been specified in bovine chromosome 19 by the analysis of F2 population which derived from of Japanese Black and Limousin breeds for genetic analysis. The FASN gene is located at a position strongly linked to the trait in the above region. Thus, the inventors have estimated from the function of the gene that the gene might be probably involved in fatty acid composition. Therefore, for analyzing the above gene, the entire cDNA sequence of FASN gene has been determined with respect to four cattle in total (i.e., two cattle of Japanese Black and two cattle of Limousin breeds), which are (P) generations of F2 populations (progenitor generations), and the differences among the genes have been investigated in detail.

Therefore, the single nucleotide polymorphisms (SNPs) at two positions represented on the bottom of FIG. 1 are those firstly observed in these four cattle. Hereinafter, these single nucleotide polymorphisms (SNPs) at two positions will be referred to as base <1> and base <2> as described below in the order from the 5' direction, respectively.

<1> The 16,024th base corresponding to a polymorphic site, which is either adenine (A) or guanine (G), in the base sequence represented by SEQ ID NO. 1 of the sequence list.

<2> The 16,039th base corresponding to a polymorphic site, which is either thymine (T) or cytosine (C), in the base sequence represented by SEQ ID NO. 1 of the sequence list.

In the base sequence represented by SEQ ID NO. 1 of the sequence list, each of the bases of the above two polymorphic sites is represented by universal code "r" or "y".

Note that, the numbers appended to base <1> and base <2> represent those corresponding to the numbers of the respective nucleotides counted from the first nucleotide of the genomic DNA sequence of the FASN gene represented by SEQ ID. NO. 1 of the sequence list.

On the other hand, the cDNA sequence does not contain any intron portion. It is in a state where only exon portions are connected to one another. Thus, the number of the respective bases corresponding the above bases <1> and <2> in the cDNA sequence of the FASN gene are obviously different from the numbers described in the above <1> and <2>, respectively.

Therefore, in the determination method of the present invention, when cDNA of cattle provided as a target of determination is used as a determination sample, the numbers indicating the respective position of the above bases <1> and <2> should be interpreted by counting in consideration of the intron sequence upstream in exon 34.

The sequence represented by SEQ ID NO. 1 of the sequence list is the genomic DNA sequence of FASN gene isolated from any of European cattle breeds, which has been investigated by the authors of Non-patent Document 3. In contrast, any of other cattle breeds may have a deletion, an insertion, or the like of one to several bases by mutation or the like in the sequence represented by SEQ ID NO. 1. In this case, the number indicating the respective position of the above bases <1> and <2> should be interpreted by counting in consideration of the deletion, insertion, or the like of such a base.

As illustrated in FIG. 1, it was found that both the above bases <1> and <2> are contained in exon 34 and also contained in an open-reading frame.

It was recognized that the substitution of an encoded amino acid would occur depending on whether the base <1> was adenine (A) or guanine (G). If the base <1> is adenine (A), then the encoded amino acid is threonine (Thr). If it is guanine (G), then the encoded amino acid is alanine (Ala).

In addition, it was also recognized that the substitution of an encoded amino acid would occur depending on whether the base <2> was thymine (T) or cytosine (C). If the base <2> is thymine (T), then the encoded amino acid is triptophan (Trp). If it is cytosine (C), then the encoded amino acid is arginine (Arg).

In this way, the substitution of each base <1> and <2> will cause the substitution of amino acids.

Further, the results of multiple genetic analyses have revealed that single nucleotide polymorphisms (SNPs) of the above bases <1> and <2> were not independent from each other but essentially linked together:

(i) if the above base <1> is adenine (A), then the above base <2> is thymine (T); and (ii) if the above base <1> is guanine (G), then the above base <2> is cytosine (c). The inventors will represent these two different haplotypes by 1-letter codes of encoded amino acids depending on the substitution of the respective bases. In other words, the haplotype (i) is referred to as a threonine (Thr=T)-triptophan (Trp=W) type (TW type), and the haplotype (ii) is referred to as an alanine (Ala=A)-arginine (Arg=R) type (AR type).

Note that, exceptionally, an individual having a combination of base <1> and base <2> which is different from the above description may be present. In the base sequence of FASN gene as described in Non-patent Document 3, a portion corresponding to the above base <1> was adenine (A) homozygote and a portion corresponding to the above base <2> was cytosine (C) homozygote. Such a case has not been found within the range of investigation by the inventors, so any relationship with the feature in the case of having these haplotypes has not been confirmed.

Therefore, if a cattle having such haplotypes exist, then the amount of the fatty acid content in intramuscular fat of beef cannot be determined.

However, the inventors carried out the typing of FASN genotype on samples of more than 1,000 cattle in total of various ox populations of Japanese Black and Holstein breeds, Japanese Black fattening cattle populations, and foreign breed populations which are domestically bred for beef. However, there is no case where an individual having recombination between base <1> and base <2> was detected. Thus, even though it does not mean that the individual does not exist at all, it seems that the possibility of detecting cattle having such a recombinant FASN genotype may be extremely low in Japan (the authors of Non-patent Document 3 are members of a foreign research group, so it is quite unlikely that the members have determined the base sequence of Japanese domestic cattle and registered the sequence).

The cattle to be provided as the determination subjects (samples) of the present invention are preferably those bred in Japan, that is, those born and grown in Japan. Note that, the inventors have only investigated cattle bred in Japan, so the frequency or the like of FASN genotype of foreign breeds bred abroad is still unknown, but the foreign breeds bred abroad can also be provided as a determination subject (sample) of the present invention when the haplotype thereof is identical with the type observed in Japan (i.e., TW type or AR type).

In addition, as describe above, any case of the recombination between base <1> and base <2> being occurred has not been detected. In the present invention, therefore, even though the FASN genotype can be determined by determination of base <1> or base <2>, it is preferable to determine both base <1> and base <2> at once.

In this way, two haplotypes have been found with respect to the genotype of FASN gene. As a result of further investigation, in particular, the inventors have found a significant relationship between the genotype of the above FASN gene and the amount of the oleic acid content among fatty acids in bovine intramuscular fat.

In other words, the inventors have found a significant difference between the above "TW type" and "AR type" with respect to the contents of fatty acids such as oleic acid in bovine intramuscular fat. A homozygote of TW-type FASN gene (TW/TW), a heterozygote of TW-type/AR-type FASN gene (TW/AR), and a homozygote of an AR-type FASN gene (AR/AR) showed higher values in the stated order with respect to the ratio of oleic acid contents, the detailed results of which will be also explained in examples described later.

Therefore, in the present invention, the amount of the fatty acid content in bovine intramuscular fat can be determined by determining base <1> and/or base <2> in the FASN gene of the cattle (the target of determination) and determining whether the genotype is any of the above TW/TW type, TW/AR type, or AR/AR type.

Fatty acids which can be determined by the present invention are not particularly limited, so they may be unsaturated fatty acids and saturated fatty acids. Examples of the unsaturated fatty acids include mono unsaturated fatty acids with 18 carbon atoms, such as oleic acid, elaidic acid, and vaccenic acid. Examples of the saturated fatty acids include those with 14 carbon atoms such as myristic acid, and those with 16 carbon atoms such as palmitic acid.

As described above, oleic acid is the most abundant fatty acid among those contained in bovine intramuscular fat and suggested to be associated with the eating quality of beef. Therefore, the cattle with FASN gene of genotype TW/TW can be evaluated as one having meat quality with a good eating quality compared with the AR/AR type cattle.

In this way, the investigation of the genotype of FASN gene makes it possible to determine whether cattles are those from which beef with a more excellent eating quality will be obtained in addition to determine the fatty acid composition in bovine intramuscular fat.

Note that, for example, the contents of various fatty acids can be determined by the following method.

40 ml of a methanol chloroform solution is added to about 1 g of a beef sample and then extracted by shaking for 7 minutes after homogenization. After that, the supernatant is dried under reduced pressure with a rotary evaporator, thereby obtaining a lipid sample.

Subsequently, according to the standard oil and fat analytical test method, the sample is saponified and then methyl-esterified. In other words, a 1-N potassium hydroxide methanol solution is added to the sample and then refluxed and heated on a water bath to be saponified, followed by methylation with the addition of a boron trifluoride methanol reagent. The sample is dissolved into hexane. Then, the sample is separated, and dehydrated with anhydrous sodium sulfate, followed by being subjected to gas chromatography.

Note that, the conditions of gas chromatography are as follows:

(Analytical Conditions of Gas Chromatography)

Column: CP-Sil88Wcot 0.25 mm×50 m

Carrier gas: helium

Injection temperature: 220° C.

Column temperature: 160° C. constant temperature

Detection: FID

In the determination method of the present invention, a method of investigating the genotype of FASN gene is not particularly limited. Thus, any of the conventional methods capable of directly or indirectly investigating whether the above base <1> on the FASN gene is adenine <A> or guanine <G> and whether the above base <2> is thymine (T) or cytosine (C) can be applied.

A method of investigating the genotype of FASN gene by testing the above bases <1> and <2> with a use of a restriction fragment length polymorphism (PCR-RFLP) method is most simple and extremely precise. Therefore, this method will be described briefly in the following description.

(2) Method of Determining Genotype of FASN Gene by PCR-RFLP Method

The PCR-RFLP method is one for detecting the presence or absence of cleavage with a restriction enzyme, that is, the presence or absence of mutation, by amplifying a gene region containing a mutation site to be detected by the PCR method, digesting the PCR product by the restriction enzyme that recognizes the mutation site, and investigating the molecular weight of a DNA fragment by electrophoresis.

At first, a gene sample is prepared from a bovine subject.

The gene sample to be provided for the determination may be genomic DNA or cDNA. In the case of genomic DNA, DNA may be purified and extracted in accordance with common methods from any of the organs, tissues, and cells (including cells in the blood and the amniotic fluid and cultured cells from collected tissues or the like) of a bovine subject (subject may be one before or after the slaughter). In the examples described later, the genomic DNA is prepared from the muscle tissue. In the case of cDNA, the cDNA may be synthesized with reverse transcriptase after purifying and extracting mRNA in accordance with common methods from any of the organs, tissues, and cells (including cells in the blood and the amniotic fluid and cultured cells from collected tissues or the like) of a bovine subject (subject may be one before or after the slaughter).

Next, for identifying bases in single nucleotide polymorphisms (SNPs) (SNP typing), the PCR method is carried out using the genomic DNA or cDNA prepared by the above method as a template and a gene region containing the above base <1> and/or the above base <2>, preferably both bases at two positions, i.e. the above base <1> and the above base <2>, is then amplified. Subsequently, the resulting amplified fragment is digested with an appropriate restriction enzyme and the genotype of FASN gene is then determined by the presence or absence of the cleavage thereof.

The respective conditions, reagents, primers, restriction enzymes, and the like used in the above PCR method are not particularly limited. Hereinafter, the conditions and the like used in the examples described later will be explained by dividing two cases, one using genomic DNA as a gene sample and the other using cDNA as a gene sample.

[A] In the Case of Using Genomic DNA as Gene Sample

A PCR reaction solution may be a solution of 20 ng of genomic DNA added with 0.25 unit of AB gene Taq polymerase, 1.5 μl of 10×Taq polymerase buffer, 1.25 μl of 10-mM dNTP mix, 0.25 μl of forward primer (6.25 pmol), and 0.25 μl of reverse primer (6.25 pmol) and then added with ultrapure water to make 15 μl of the solution.

Here, the above forward primer and reverse primer may be oligonucleotides which can specifically amplify a gene region containing the above base <1> and/or the above base <2>, preferably both the above base <1> and the above base <2>.

For example, the forward primer is a part of the base sequence represented by SEQ ID NO. 1 of the sequence list and may be an oligonucleotide consisting of any base sequence located at the 5' direction side from a mutation site to be detected. In addition, the reverse primer is a part of the base sequence represented by SEQ ID NO. 1 of the sequence list and may be an oligonucleotide consisting of a base sequence complementary to any base sequence located at the 3' direction side from a mutation site to be detected.

The above primer pair is preferably consisting of 15 to 50 nucleotides, and more preferably 18 to 27 nucleotides. In addition, the length of the amplified product obtained by the PCR method is, but not particularly limited to, preferably consisting of 100 to 500 bases.

Specifically, forward primer (FASN_F) represented by SEQ ID NO. 3 of the sequence list and reverse primer (FASN_R) represented by SEQ ID NO. 4 of the sequence list can be exemplified. The forward primer is prepared from the base sequence in FASN gene exon 34, while the reverse primer is prepared from the base sequence in FASN gene exon 35.

The reaction conditions of PCR may be defined as; firstly (1) 94° C. for 4 minutes, next (2) a cycle of 94° C. for 30 seconds, 60° C. for 30 seconds, and 72° C. for 30 seconds being repeated 35 times, followed by finally (3) 72° C. for 7 minutes.

A 336-bp PCR-amplified product can be obtained by the above PCR method using a pair of primers represented by SEQ ID NO's. 3 and 4 of the sequence list.

Restriction enzymes and the like used in the detection of polymorphism vary as described below depending on which of the above base <1> or <2> is determined.

[A-1] In the Case of Determining the Above Base <1>

In the case that the above base <1> is adenine and the PCR-amplified product obtained as described above is treated with restriction enzyme HhaI, the polymorphic site of the above base <1> in the PCR product is not cleaved by the restriction enzyme. In this case, an encoded amino acid corresponds to threonine, so the genotype can be determined as of a T type.

On the other hand, in the case that the above base <1> is guanine, the polymorphic site of the above base <1> in the PCR product is cleaved by the above restriction enzyme. In this case, an encoded amino acid corresponds to alanine, so the genotype can be determined as of an A type.

[A-2] In the Case of Detecting the Above Base <2>

In the case that the above base <2> is thymine and the PCR-amplified product obtained as described above is treated with restriction enzyme NciI, the polymorphic site of the above base <2> in the PCR product is not cleaved by the restriction enzyme. In this case, an encoded amino acid corresponds to triptophan, so the genotype can be determined as of a W type.

On the other hand, in the case that the above base <2> is cytosine, the polymorphic site of the above base <2> in the PCR product is cleaved by the above restriction enzyme. In this case, an encoded amino acid corresponds to arginine, so the genotype can be determined as of an R type.

[B] In the Case of Using cDNA as Gene Sample

In a manner similar to that of genomic DNA, a PCR reaction solution may be a solution of 20 ng of cDNA added with 0.25 unit of AB gene Taq polymerase, 1.5 μl of 10×Taq polymerase buffer, 1.25 μl of 10-mM dNTP mix, 0.25 μl of forward primer (6.25 pmol), and 0.25 μl of reverse primer (6.25 pmol) and then added with ultrapure water to make 15 μl of the solution.

In this case, the same primers as those used for the genomic DNA may be also used. In other words, the primers may be those that can specifically amplify a gene region containing the above base <1> and/or the above base <2>, preferably both the above bases <1> and <2>.

Specifically, the forward primer used may be an oligonucleotide consisting of the base sequence represented by SEQ ID NO. 3 of the sequence list and the reverse primer used may be an oligonucleotide consisting of the base sequence represented by SEQ ID NO. 4.

As described above, the forward primer represented by SEQ ID NO. 3 of the sequence list is prepared from the base sequence in exon 34, and the reverse primer represented by SEQ ID NO. 4 of the sequence list is prepared from the base sequence in exon 35. In the case of using cDNA as a gene sample, a PCR-amplified fragment thereof is shorter than that of one using genomic DNA as a gene sample because intron portions are cut out by splicing.

Therefore, if the genomic DNA is remained in cDNA without digestion, two amplified fragments can be detected on one lane after the PCR reaction. In other words, in the case of using cDNA as a gene sample, it is possible to confirm the contamination of genomic DNA by carrying out PCR using each of the above forward and reverse primers.

In a manner similar to that of the genomic DNA, the reaction conditions of PCR may be defined as; firstly (1) 94° C. for 4 minutes, next (2) a cycle of 94° C. for 30 seconds, 60° C. for 30 seconds, and 72° C. for 30 seconds being repeated 35 times, followed by finally (3) 72° C. for 7 minutes.

A 226-bp PCR-amplified product can be obtained by the above PCR method using a pair of primers represented by SEQ ID NO's. 3 and 4 of the sequence list.

FIG. 1 schematically illustrates white arrows that represent the positions of respective primers represented by SEQ ID NO. 3 and SEQ ID NO. 4 to be used in a PCR reaction. The right pointing white arrow represents a forward primer and the left pointing white arrow represents a reverse primer.

In the case of using genomic DNA as a gene sample, the whole fragment (including primer portions) sandwiched between these white arrows is amplified. In the case of using cDNA as a gene sample, on the other hand, an intron portion sandwiched between exon 34 and exon 35 is cut out, so a fragment shorter than one obtained by using the genomic DNA as a gene sample is amplified.

Restriction enzymes used in the detection of polymorphism vary depending on which of the above base <1> or <2> is determined. The enzymes may be the same as those described in the sections [A-1] and [A-2] of the above section [A] and the treatment method and detection method may be carried out similarly as in the cases of the section [A]. The results may be also determined similarly as in the cases of the section [A].

Note that, in any of the case of using genomic DNA and the case of using cDNA as a gene sample, PCR-RFLP treatment can be carried out as described below. That is, in the case of using HhaI, a reaction solution is prepared such that 0.5 μl of buffer, 1 μl of BSA, and 5 U of HhaI are added to 5 μl of the PCR product and the mixture is then added with ultrapure water to make 10 μl of the reaction solution. In the case of using NciI, a reaction solution is prepared such that 0.5 μl of buffer and 5 U of NciI are added to 5 μl of the PCR product and the mixture is then added with ultrapure water to make 10 μl of the reaction solution. Subsequently, these reaction solutions are reacted overnight at 37° C. Electrophoresis is carried out under the conditions of using 2% agarose gel at 100 V for 30 minutes.

Figure 2:
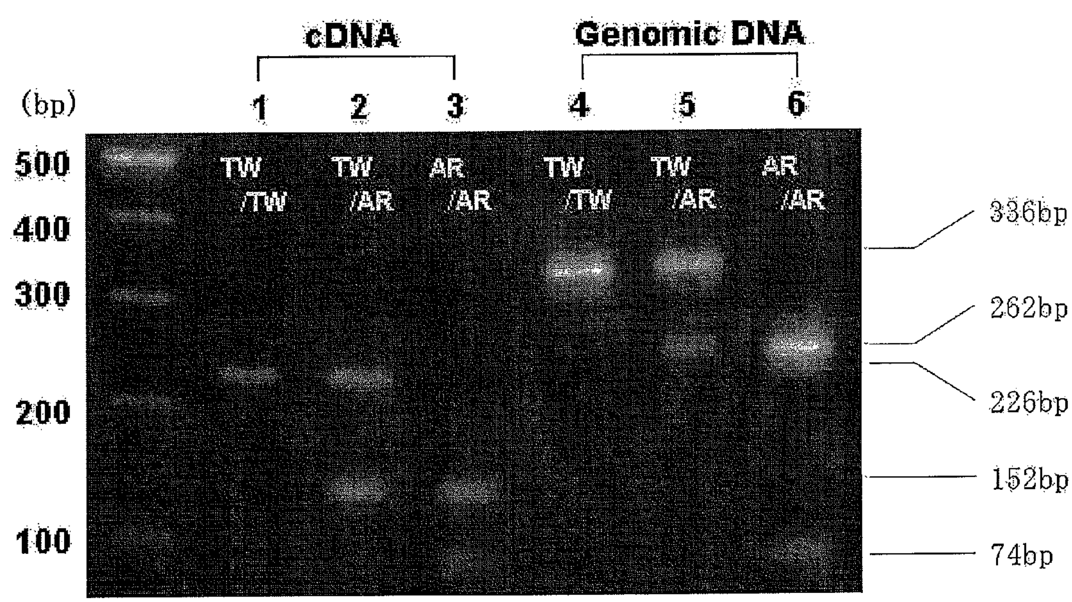
FIG. 2 is a diagram for illustrating the results of electrophoresis in the determination method of the present invention using the PCR-RFLP method.

FIG. 2 illustrates the results of the electrophoresis. These results are those obtained by detecting the above base <1> using a pair of primers represented by SEQ ID NO's. 3 and 4 in the sequence list and HhaI. Lanes 1 to 3 represent the results obtained using cDNA as a gene sample and lanes 4 to 6 represent the results obtained using genomic DNA as a gene sample.

As shown in lanes 1 to 4 in the figure, when only large molecular-weight bands (226 bp and 336 bp, respectively) are appeared, the above base <1> is a homozygote of adenine. Thus, it can be determined as a T-homo type when represented by the encoded amino acid. In addition, as shown in lanes 3 and 6 in the figure, when only small molecular-weight bands (74 bp, 152 bp, and 262 bp, respectively) are appeared, the above base <1> is a homozygote of guanine. Thus, it can be determined as an A-homo type when represented by the encoded amino acid. Further, when both the above large molecular-weight and small molecular-weight bands are appeared as shown in lanes 2 and 5 in the figure, the genotype can be determined as a heterozygote.

In this way, according to the PCR-RFLP method, the genotype of FASN gene can be simply investigated with high accuracy.

In addition, as described above, two single nucleotide polymorphisms (SNPs) of FASN gene are very proximal to each other with an interval of only 14 bases. Therefore, most of the haplotypes formed by the nucleotides may be considered to be fixed. Thus, when one mutation is detected, a type of the other mutation can be naturally determined.

However, as described above, the possibility of the haplotypes other than TW type and AR type being present, i.e., the possibility of an individual causing a recombination between two single nucleotide polymorphisms (SNPs) being present, cannot be completely denied. Thus, in the determination of the genotype of FASN gene, the accuracy can be more enhanced by confirming both single nucleotide polymorphisms (SNPs) at two positions.

(3) Modified Embodiment of Determination Method of the Present Invention

As described above, the determination method of the present invention is not limited to the PCR-RFLP method of the above section (2). For instance, even when the determination is carried out by the PCR-RFLP method, each of the reaction conditions, reagents, primers, restriction enzymes, and the like to be used may be modified in various ways.

In the determination method of the present invention, obviously, any of the methods other than the PCR-RFLP method may be used. Any of various conventional methods, such as a method of detecting a point mutation on a base sequence and a method of determining a base in a single nucleotide polymorphism (SNP) (SNP typing), can be applied as far as it is possible to directly or indirectly detect the above base <1> and/or <2> on the FASN gene.

One example is a determination method, which is the one using a PCR apparatus capable of carrying out both the mutation detection and the real-time PCR (quantitative PCR), provided with a thermal cycler and a fluorescence detector (example of PCR apparatus includes "light-cycler system" (trade name) developed by Roche Diagnostics, Co., Ltd).

In this method, a primer pair for amplification of a gene region containing the above base <1> and/or the above base <2> by the PCR method, a mutation detection probe with the 3' end labeled with a fluorescent substance, Fluorescein Iso Thio Cyanate (FITC), and an anchor probe with the 5' end labeled with a fluorescent substance, Light Cycler-Red (LC-RED) and the phosphorylated 3' end are properly designed and used. Alternatively, these substances may be ordered to be prepared by an appropriate vendor.

Subsequently, these primers, mutation detection probe, and anchor probe are mixed with appropriate reagents including DNA synthase together with a DNA sample from the test subject, followed by carrying out an amplification reaction using the light-cycler system. The mutation detection probe used in this case is designed to cover a mutated portion of interest (i.e., base <1> and/or base <2>). Thus, the denaturation temperature of DNA with a mutation is different from that of DNA without mutation, so such a difference can be used in the detection of polymorphism.

The probe for detecting mutation which can be used in the above determination method may be any of nucleotide probes which can be specifically bound to a gene region containing the above base <1> and/or the above base <2> and labeled with a fluorescent substance, FITC, on the 3'end thereof. Among them, a probe having 20 to 30 nucleotides is preferable. The sequence of the nucleotide probe is, for example, a part of the base sequence represented by SEQ ID NO. 1 of the sequence list. In addition, a sequence containing the above base <1> and/or the above base <2> or the complementary sequence thereof can be used.

Additionally, as one of the embodiments of the determination method of the present invention, a determination method using a gene-polymorphism-detecting instrument such as a DNA chip, and a method using a point-mutation detection method such as a single-strand conformation polymorphism (PCR-SSCP) are mentioned.

Note that, the term "DNA chip" means a synthetic-type DNA chip in which a synthesized oligonucleotide is mainly used as a probe, but includes an attached-type DNA microarray in which cDNA such as PCR product or the like is used as a probe.

For determining the above base <1> and/or the above base <2> using a DNA chip, the DNA chip (or the same kind of a device) is prepared such that a probe for determining any of these bases is arranged on a base, the probe and a gene sample from the bovine subject are hybridized with the use of DNA chip or the like, and then a SNP-typing is carried out on the basis of the presence or absence of such a hybridization signal.

The probe used in the above DNA chip or the like may be a nucleotide probe specifically bound to a gene region containing the above base <1> and/or the above base <2>. Specifically, a part of the base sequence represented by SEQ ID No. 1 of the sequence list and a base sequence containing the above base <1> and/or the above base <2> of the polymorphic site or a complementary sequence thereof can be used. Among them, a probe having 20 to 30 nucleotides is preferable.

In addition, in the determination method of the present invention in which the PCR-RFLP method is used, any of other amplification methods (such as a rolling circle amplification (RCA) method) may be used instead of the PCR method. Further, after the DNA amplification, instead of the RFLP method, the base sequence of the amplified fragment may be directly determined by a base sequence determination apparatus (DNA sequencer) or the like to carry out the typing of single nucleotide polymorphisms (SNPs).

Note that, with respect to the base sequence of FASN gene, there is a possibility of causing other mutations among cattles belonging to European cattles (*Bos taurus*) in addition to the single nucleotide polymorphisms (SNPs) of the above bases <1> and <2>. In other words, strictly speaking, there is a possibility of the presence of cattle having a FASN gene sequence different from the base sequence represented by SEQ ID NO. 1 of the sequence list. Even in the case of such cattles, it is possible to determine the amount of the fatty acid content in intramuscular fat by investigating the genotype of FASN gene using the determination method of the present invention as described above. In addition, it is also possible to determine the eating quality of beef on the basis of the result of the above determination.

Further, if the bovine subject is one artificially created by genetic recombination or the like, mutation may be also artificially introduced into the FASN gene. In this case, however, the determination method of the present invention can be also applied similarly as mentioned above.

The gene sample prepared from the bovine subject may be either DNA or RNA. In addition, a method of preparing the gene sample is not particularly limited and may be carried by common procedures.

(4) Application Field of the Present Invention (Utility)

The determination method of the present invention is a method of determining fatty acid composition, particularly the amount of the oleic acid content in bovine intramuscular fat on the basis of the genotype of FASN gene, and is available in the fields of livestock industries (such as the raising, reproduction, breeding, and improvement of cattles), production and processing of beef, and the like.

As described above, the most abundant fatty acid is oleic acid among the fatty acids in bovine intramuscular fat. In particular, it is known that the Japanese Black beef has the content of oleic acid significantly higher than that of the foreign breeds. It suggests that a good eating quality of beef which Japanese likes may be greatly effected.

Therefore, the determination method of the present invention is able to evaluate whether a beef breed (beef cattle) such as Japanese Black, or a dairy breed such as Holstein to be supplied for meat, is a cattle having the meat quality with a good eating quality. In addition, the eating quality of beef can be improved based on this evaluation result, even though such an improvement has been almost impossible, by cross-breeding of cattles having meat qualities with excellent eating quality classified on the basis of the genotype with each other, or the like.

Further, even in the case of carrying out a selective breeding of cattle with genetic recombination or the like or a useful genetic experiment in the field of livestock industry or the like, the determination method of the present invention is available for the screening of intended cattle, sperms, fertilized eggs, and the like. In addition, the present invention is applicable to prenatal diagnosis judgment. For instance, cells derived from a bovine fetus are collected from the amniotic fluid of the uterus, and then a gene sample is prepared from the cells so as to be able to determine whether the cattle can produce beef with more excellent eating quality.

Examples

Hereinafter, the present invention will be described in more detail with reference to examples and the like.

In the examples described below, a gene sample used was genomic DNA prepared by common procedures from the muscle tissue of a bovine subject (such as Japanese Black, Limousin, Hereford, Angus, Holstein, or crossbred cattles thereof) and the determination was then carried out by the PCR-RFLP method described above.

In addition, in the examples described below, the genotype (haplotype) of FASN gene was determined whether it is a TW type or an AR type by investigating the above base <1>.

Reagents, reaction conditions, and the like used in the PCR method are as described above, so the description thereof will be omitted. Note that, a pair of primers used in the PCR method was one represented by SEQ ID NO's. 3 and 4 of the sequence list.

(1) Relationship Between FASN Genotype and Various Fatty Acid Contents

Table 1 below represents the results of the determination of the genotype of FASN gene in F2 populations for genetic analysis of Japanese Black and Limousin breeds described above and also represents the mean and standard deviations of fatty acid contents in intramuscular fat with respect to the genotype of each of FASN genes. Note that, the genotype was represented by a haplotype formed of the type of an amino acid encoded according to the substitution of each base.

Note that, in Table 1, C14:0 represents myristic acid, C16:0 represents palmitic acid, and C18:1 represents oleic acid.

Here, the contents of various fatty acids were determined by the following procedures:

About 1 g of a beef sample was taken into a glass centrifugation tube and then added with 20 ml of saline and 40 ml of a methanol chloroform solution (stock solution prepared by mixing chloroform, methanol, and butylhydroxy toluene at amounts of 2 liters, 1 liter, and 15 mg, respectively), followed by homogenization with a homogenizer. The resulting mixture was poured onto a separatory funnel and then stirred for 7 minutes and then filtrated through anhydrous sodium sulfate. The resultant was dried with an evaporator under reduced pressure, thereby obtaining a lipid sample.

Subsequently, 5 ml of a 1-N potassium hydroxide methanol solution was added to the sample, refluxed and heated on a water bath at 95° C. for 1 hour to be saponified, added with 10 ml of diethyl ether, and stirred, followed by discarding the supernatant. Then, 1 ml of a 6-N sulfuric acid and 10 ml of petroleum ether were added and then stirred, followed by transferring the supernatant into another tube. Then, the residue was dried under the reduced pressure with an evaporator and then added with 1 ml of a boron trifluoride methanol solution, and then refluxed and heated on a water bath at 95° C. for 5 minutes to be methylated. After transferred into hexane, the resultant was separated, and dehydrated with anhydrous sodium sulfate, followed by being subjected to gas chromatography to carry out the determination of fatty acid composition.

Note that, the conditions of gas chromatography were as follows:

(Analytical Conditions of Gas Chromatography)

Column: CP-Sil88Wcot 0.25 mm×50 m

Carrier gas: helium

Injection temperature: 220° C.

Column temperature: 160° C. constant temperature

Detection: FID

TABLE 1

| FASN genotype | Number of cattle | C14:0 content (%) Mean value | C16:0 content (%) Mean value | C18:1 content (%) Mean value |
|---|---|---|---|---|
| TW/TW | 66 | $3.33 \pm 0.42^{a}$ | $27.72 \pm 1.76^{d}$ | $45.81 \pm 2.37^{g}$ |
| TW/AR | 87 | $3.65 \pm 0.45^{b}$ | $28.43 \pm 2.22^{e}$ | $44.62 \pm 2.70^{h}$ |
| AR/AR | 27 | $4.49 \pm 0.64^{c}$ | $29.42 \pm 2.11^{f}$ | $42.81 \pm 2.25^{i}$ |

As a result of performing a one-way analysis of variance with FASN genotype as a factor, the fatty acid content in intramuscular fat differed depending on the kind of fatty acid classified in accordance with haplotypes. The contents of the respective saturated fatty acids with 14 and 16 carbon atoms were highest in AR/AR type, followed by TW/AR type and lowest in TW/TW type. In contrast, the contents of the respective mono unsaturated fatty acid with 18 carbon atoms (oleic acid) were highest in TW/TW type, followed by TW/AR type and lowest in AR/AR type.

As stated above, it is suggested that the content of oleic acid may be associated with the eating quality of Japanese Black cattle beef. As is evident from the results, it was found that the cattle having the TW-type allele of two alleles of FASN gene showed higher oleic acid content than the cattle having the AR-type allele, while the former tended to show lower contents of other fatty acids than the latter. In other words, it was proved that the eating quality of beef can be also determined by investigating the genotype of FASN gene.

Note that, in Table 1, superscript letters: a, b and c show the significant difference with $p<3.93\times10^{-20}$; d, e and f show the significant difference with $p<0.002$; and g, h and i show the significant difference with $p<2.4\times10^{-6}$.

(2) Relationship Between FASN Genotype and the Content of Oleic Acid in the Half-Sibling Population of Japanese Black A However, the results obtained in the above section (1) were absolutely due to the breed difference between Japanese Black and Limousin (foreign beef breed). Thus, there was a need of confirming the influence of the FASN genotype on the content of oleic acid in intramuscular fat with respect to domestic Japanese Black. Therefore, among Japanese Black fattening cattle bred in Yamagata, samples were collected from half-sibling population of elite sire A and their genomic DNAs were extracted to investigate the FASN genotypes thereof.

Table 2 below represents the results of the FASN genotype determination of the samples from half-sibling population of elite sire A and the mean and standard deviations of the oleic acid contents in intramuscular fat. Note that, the measurement of the oleic acid content was carried out in a manner similar to the above section (1).

TABLE 2

| FASN genotype | Number of cattle | C18:1 content (%) Mean value |
|---|---|---|
| TW/TW | 76 | $53.05 \pm 2.09^{a}$ |
| TW/AR | 98 | $50.86 \pm 2.55^{b}$ |
| AR/AR | 31 | $50.31 \pm 1.99^{c}$ |

As described above, the same tendency as one observed in the F2 population for genetic analysis in Table 1 could be also confirmed in the half-sibling population of Japanese Black elite sire A. In other words, the content of oleic acid in intramuscular fat were highest in TW/TW type, followed by TW/AR type and lowest in AR/AR type. Different superscript letters shown in Table 2 represent a significant difference with $p<22\times10^{-10}$. From these results, it was shown that the FASN genotype had an effect on the content of oleic acid in intramuscular fat of Japanese Black.

Note that, it was also confirmed that the half-sibling sample of elite sire A showed a significant relationship with the FASN genotype with respect to plural fatty acids other than oleic acid similar to the results of the F2 population for genetic analysis shown in Table 1 as described above. In contrast, the above Table 2 only indicates the relationship with the content of oleic acid which is suggested to be particularly associated with the eating quality of beef.

(3) Relationship Between FASN Genotypes and Oleic Acid Contents in Half-Sibling Populations of Three Japanese Black Sires Subsequently, samples of Japanese Black fattening cattle populations bred in Yamagata were further collected, and as a result, samples from half-sibling population of three elite sires, which were different from the above elite sire A, could be secured. These samples were also investigated with respect to their FASN genotypes by extraction of their respective genomic DNAs in a manner similar to that of the above section (1).

Table 3 below represents the results of the FASN genotype determination of the samples from half-sibling population of three elite sires and the mean and standard deviations of the oleic acid contents in intramuscular fat.

TABLE 3

| FASN genotype | Number of cattle | C18:1 content (%) Mean value |
|---|---|---|
| TW/TW | 205 | 53.91 ± 2.19[a] |
| TW/AR | 161 | 53.02 ± 2.64[b] |
| AR/AR | 0 | — |

As is evident from Table 3, the same tendency as one observed in the above sections (1) and (2) could be also confirmed. However, any individual having a homozygous AR type could not be found in this population. It was found that this was because all fathers of the half-sibling populations of three elite sires used accidentally showed their respective FASN genotypes as homozygous TW type. Different superscript letters shown in Table 3 represent a significant difference with $p<5.7\times10^{-4}$.

Note that, although it was confirmed that there was a significant relationship with the FASN genotype with respect to plural fatty acids other than oleic acid, the above Table 3 only indicates the relationship with the content of oleic acid which is suggested to be particularly associated with the eating quality of beef.

In view of the above, as shown in Tables 1 to 3, it becomes clear that the FASN genotype have an effect on the amount of the oleic acid content in intramuscular fat of Japanese Black.

(4) Difference in Breeds with Respect to Genotype Frequency and Gene Frequency of FASN Gene Next, difference among breeds were investigated with respect to the genotype frequency represented by the haplotype formed of two single nucleotide polymorphisms (SNPs) accompanied with the amino acid substitution of FASN gene and the allele frequency similarly represented by the haplotype.

In other words, genomic DNA extracted from the sire frozen semen of cattles of each breed shown in Table 4 below according to any common procedures was used as a sample and the investigation of FASN genotype was carried out in a manner similar to the above section (1). In addition, the sire frozen semen of Japanese Black and Holstein breeds used was one distributed in Japan. The results are shown in Table 4.

TABLE 4

| | Genotype frequency | | | Gene frequency | | |
|---|---|---|---|---|---|---|
| Breed name | Haplotype | n | % | Haplotype | n | % |
| Japanese Black | TW/TW | 31 | 47.0 | TW | 88 | 66.7 |
| (66 cattle) | TW/AR | 26 | 39.4 | AR | 44 | 33.3 |
| | AR/AR | 9 | 13.6 | | | |
| Holstein | TW/TW | 3 | 4.3 | TW | 24 | 17.1 |
| (70 cattle) | TW/AR | 18 | 25.7 | AR | 116 | 82.9 |
| | AR/AR | 49 | 70.0 | | | |
| Aberdeen Angus | TW/TW | 0 | 0.0 | TW | 2 | 1.5 |
| (65 cattle) | TW/AR | 2 | 3.1 | AR | 128 | 98.5 |
| | AR/AR | 63 | 96.91 | | | |
| Hereford | TW/TW | 0 | 0.0 | TW | 2 | 7.1 |
| (14 cattle) | TW/AR | 2 | 14.3 | AR | 26 | 92.9 |
| | AR/AR | 12 | 85.7 | | | |

As described above, it was revealed that large differences in both FASN genotype frequency and gene frequency were found among Japanese Black, Holstein (dairy breed), and foreign beef breeds. In other words, the FASN haplotype having an effect of increasing the content of oleic acid in intramuscular fat (i.e., TW type) was broadly distributed in Japanese Black compared with other breeds.

In general, it is widely recognized that the meat of Japanese Black has excellent eating quality which Japanese likes in comparison with Holstein and foreign beef breeds, and it is also suggested that the amount of the oleic acid content contributes to the fact. Differences in FASN genotype frequency and gene frequency described above support that the Japanese Black can produce beef with excellent eating quality.

The invention claimed is:

1. A method of predicting an amount of fatty acid content in bovine intramuscular fat, wherein the fatty acid is oleic acid, myristic acid or palmitic acid, comprising the steps of:

(a) determining base <1> and base <2> described below:

<1> a 16,024$^{th}$ base corresponding to a polymorphic site which is either adenine (A) or guanine (G) shown in a base sequence represented by SEQ ID NO:1 of a sequence list; and <2> a 16,039$^{th}$ base corresponding to a polymorphic site which is either thymine (T) or cystosine (C) shown in the base sequence represented by SEQ ID NO:1 of the sequence list;

(b) determining the genotype of fatty acid synthase defined by the base <1> and the base <2>; and (c) predicting that the contents of the oleic acid are highest in TW/TW genotype, followed by TW/AR genotype and lowest in AR/AR genotype, and that the contents of the myristic acid and palmitic acid are highest in AR/AR genotype, followed by TW/AR genotype and lowest in TW/TW genotype.

2. The determination method according to claim 1, wherein the determination of the base <1> and the base <2> is carried out using a DNA chip.

3. The determination method according to claim 1, wherein the determination of the base <1> and the base <2> is carried out using a polymerase chain reaction device equipped with a thermal cycler and a fluorescence detector.

4. The determination method according to claim 1, wherein the cattle is a beef breed.

5. The determination method according to claim 1, wherein the cattle is a dairy breed which is also available for a beef breed.

6. A method of predicting an amount of fatty acid content in bovine intramuscular fat on the basis of the genotype of fatty acid synthase defined by base <1> and base <2> described below:

<1> a 16,024th base corresponding to a polymorphic site which is either adenine (A) or guanine (G) shown in a base sequence represented by SEQ ID NO. 1 of a sequence list; and <2> a 16,039th base corresponding to a polymorphic site which is either thymine (T) or cytosine (C) shown in the base sequence represented by SEQ ID NO. 1 of the sequence list, comprising the steps of:

(a) amplifying a gene region containing the base <1> and the base <2> by a gene amplification reaction using as a template genomic DNA or cDNA prepared from a bovine subject;

(b) digesting an amplified fragment obtained in the step (a) with restriction enzymes, and determining a genotype of fatty acid synthase based on the presence or absence of cleavage; and (c) predicting that contents of oleic acid are highest in TW/TW genotype, followed by TW/AR genotype and lower in AR/AR genotype, and that contents of myristic acid and palmitic acid are highest in AR/AR genotype, followed by TW/AR genotype and lowest in TW/TW genotype.

7. The determination method according to claim 6, wherein:

the gene amplification reaction in the step (a) is carried out by a polymerase-chain reaction using a forward primer consisting of a base sequence represented by SEQ ID NO. 3 of the sequence list and a reverse primer consisting of a base sequence represented by SEQ ID NO. 4 of the sequence list; and the restriction enzymes used in the step (b) are HhaI and NciI.

* * * * *

SEQUENCE LISTING

```
<160> NUMBER OF SEQ ID NOS: 4

<210> SEQ ID NO 1
<211> LENGTH: 19760
<212> TYPE: DNA
<213> ORGANISM: Bos Taurus
<220> FEATURE:
<221> NAME/KEY: misc_feature
<222> LOCATION: (9198)..(9198)
<223> OTHER INFORMATION: unsure
<220> FEATURE:
<221> NAME/KEY: misc_feature
<222> LOCATION: (11682)..(11682)
<223> OTHER INFORMATION: unsure

<400> SEQUENCE: 1

ccgcggccgt cgcggaaggc ccctgcaggc ctcggagcgt cccccgggtt cccgcactcg      60

ccccgggaat ttggccggca aggcaggaag gacccggggc gttgcgctgc ggtgaccgac     120

agtaaccccg cacggggcac cctcggccgg gtcaatgacc gcgcgcggcc cgcgcagagc     180

ccggggccac ccggcccatc accctatcac ctagcaacgc ccactcgagg ggcgccattg     240

ggccagcgcg cacgcctcgg gcccccgatt ggctccggct gcagagagcc acgcccccgg     300
```

```
cccggctccg ctcagcccgg atgctggccg tcaattcgaa cgcctggggg tccgtctagc    360
ccccagtgtg gccccagtat gacccccaga gtgacccaag tacgccccgt tccgtttcct    420
ccgcgcgccg tgcacacgtg gcccccgcga tcccgaaggt ggggcggccc cgggaggcgt    480
ggagcacgga acggaagttg gggggcgggg gtgacaccgt gccccgcccc agagcccccc    540
gagtccgggg cccccaaccc ggcgcccccct gggcgcgccc ccgcgcaggg tcccggctcc    600
cggcggcggc gcgccgcatc accccactgg cggcggcgcg ccttgtcccg gggcgcagcc    660
ccgacgctca ttggcctggg cggcgcagcc aagctgtcag cccatgtggc gtgtccgcac    720
ggggacgacc gcggttaaat agcgccggcg cgggcctaga gggagccaga gagacggcag    780
tagcggcctc tcctccaccg cacactccat cctcgctctc cctcagccgt tcgcacagcc    840
gcccgcgccc agaccaggta caagcggcca ggccgggccg gggtcggaag ttgcgagtcg    900
ggaacccggt cctggggcca gactggatcg ggggctgggg cgggagcaag gcggccgggc    960
tcgagcgggc gccgacggcc cgcatcctct ggccttgggt gcgcatggtt cggcgcgctg   1020
atggtgaggg ctcatctcac acagcctgcc ctggtctcgg cgtccgagcc tacggtctgg   1080
atgttcgagc cccacgagac gcccgaggct aggcggcaaa gggccctcgc gccatgccta   1140
agcccagcga ggcaggtggg cggatagcga ggggcggacg cccgggaacg ccgcgaacag   1200
ccattttggt cttggactgg gccgggcggc tgcggaccct cgagggcctg ttggagcccc   1260
cagccgccac accctcgagg gcctcctttt ccggcttggc cgccgaaccc ctccacccac   1320
ggcatcccca tgcctccggg tgcaggatag ccgtctcggc cgaccggagg gcctgagaag   1380
aggggaggga ggtggatgga ggaggcgcag ggccgtataa ggtcggctcc tccaccacgt   1440
gggctccatt tggagccccc agagttctgg ggggagagcc actcctgccg ggtgcaacct   1500
cacggcggcg cgcgcagttt cgccagcgcc gcaggggtct ccaccctttt gcctcgtccc   1560
gccggactcc gcgtgaatag caagtagggg gagaacagag cgggcgcttt ctggagaagc   1620
agccgccccg ggagctggtg cttctgggcc ggcaaagggc tctttattca gcgctggggg   1680
agggggctcc ctctgccgga acgccggggc gatcaggcca cccaaggaag acgctctctc   1740
cactcatact ttcccatgct cagagaaacc ctaaaggccc agtagttgga gagttcacca   1800
gtcatcggcg ccataaggcc ctggagcctt ggtgaaagtt tgcaggacca accttggcct   1860
tgcccacttc ctcaaacagg agccccatcc agggcccaca ggctcagggt agactaggtt   1920
cccccggtgg ggctgggaaa cctggggctg gatggacagg caggctgcac aagtaagcaa   1980
gcgcaagtcc tgaggcctcg acctgtgcaa gatgtgtggg tctgggtagt gcttgcctgg   2040
cagctgagag agtggttctc caggttggag cctgctggag gggccgtaca ggctggggct   2100
ggcccactgt gggacaggga ccaatttttc cccagagccc cgccaggcct tggcactgtt   2160
gaggagacca agctgtggtt ctggcctgga gggcagctcg agatactgag cgcagagcca   2220
gctagtccag tgtgggcact tcttaccacc accacattg ccctgtatcc ttcgcctact    2280
aaattccctg ggctacctct taacaggctg acggccaggc agtcccttcc tcagaagggt   2340
ttgggccctg cctcccacca tggggccccc tcctgagtct cctgcagcag ggctgtggtg   2400
gggtcacccc aggccaaggc caatgcccag agagcccaat gcgaggtgtt ggcaggctgg   2460
accagagtgg ggactcccct ttcccaacca ccagacatac ccttcacaaa acgttccagc   2520
gggtgcacag ccccagagct ggccatgtgg atctttgttg cagggctttc tgagctgctg   2580
ttctcagacc cttgagtggg ccagatggag gagggagttc atgaagccag ggttgggaag   2640
cagctgggtc tccagcgagg ctgtggactg gcagtgctgg ggcccaggct gactggtgtc   2700
```

cgggccccca tgccaccctc cttgcagaga gagcagccat ggaggaggtg gtgatcactg 2760
gcatgtctgg gaagctgcct gagtcggaga acctggagga gttctgggcc aatctcattg 2820
gcggtgtgga catggtgaca gatgatgaca ggcggtggaa ggccggtaag cgagcctggg 2880
gcttccccgc ctacttgaga ggttcttttc tcaccccttc tgtggacaca attctcttgg 2940
gttaccaggg agggcctgca ctccggtccc actggcagag ccaacagtca cctaaggtga 3000
ggccgtgtta tagcttcttt ctggagacgg taccagaagg ctctgggcta ggggaacgtg 3060
ggacctctgg ccagtgggct agggactgaa ctccagcctg tgggagtctg gagttctctg 3120
ggcatagcct ttgccccttt cacagaccag ggccattgct tagggtggag ccagggcaag 3180
accaggtggg tgaacacctc cagccagcca ctgcctgccc acgtgctgtc ccaggcggtc 3240
agataagaca tcaggctccc ccgggaagct ggtttgactc cctcacgccc agtagattct 3300
cccgcagagc ggctccacct gatctacagg atatgagtca gtgtggcaga gcctggctgg 3360
ccttacctgc aggccgggat ggggccaggc agaaggtctt agccaggtca ggacagtggc 3420
aggtgggagg aggcagcgct gccgctacaa gtgctctgct ctgttctggg cccatcaccc 3480
atgaggttcc ccctgggcca aagggtcccg ttcaaaagtg ggccacccat cccagggagc 3540
ttgaagctcc gtgttgcaag ccgggactcc cccccagtca atcacttagg gttatgatgt 3600
cctatgactt gatttctcca cctgtgtgtg ttccctagga ctatatggcc tgcctcggcg 3660
gtcaggcaag ctgaaggacc tgtcccggtt tgacgcttcc ttcttcgggg tccaccccaa 3720
gcaggcacac aatatggacc cccagctccg cttgctgctg gaggtcacct acgaggccat 3780
tgtggatgca ggtgggccat ctggggggct gcagagggcc agtccccaag tttcctgctg 3840
cccttcttga aaacctccct ttttgcttct aaaagcatcg tgtgttcata acaaaacatc 3900
cagaacagaa ggtgctgagg agggagcgga gccctgggct ggggccgacg aggtggggag 3960
gtgtgggcct caggcagttc aggtttcaca attgcacacc agaggaatcc cagacatgtc 4020
cgtgtcaccc cagtttcctc actccccatt gcatggctga tcttggaggc gagggcagga 4080
caccaggtgc caggcagagc aggaggcagg atctggcccc aggactttca ccctccactc 4140
ccctctgctg ggttgtgcct agccttgtaa aagtgcttca agggcacaga cttgtcccgg 4200
ggacactggg gaacatggaa attgtgctga gtgggagagg gaaggctgtc catgggggtg 4260
aggcccctca gcaggtgggc cacaggggaa cccaggacct gcctactgcc acctgtggtt 4320
tgcagggcgg gtaccctggc cttacaggtc tcttgtcttg ccgcagatgc ttagtagccc 4380
ctggggttga cccttgagtg tgccagggtc ctggacaggc cctgcctggg gggaggggcg 4440
gggaggccga ggccttccca ctgcccaggc cccagccgga gaccttggat gctgctctcc 4500
aggggcttgc cagtgtccct ccctccttcc caagcctgca cactcggctt ttgtctctct 4560
ctgtcttctt aatcttgggc cggccaaggg caggctgctt ctcagggctc atcagaccct 4620
tgccagcagt accagtgccc aggggaggta gcctggggac agtgcttgtc ctctgtcccc 4680
accgtccagc tgtctctggc ctctgcctga cccagagact ggagccccat ctggcacccc 4740
gcctgtcccc cgggccccag ttttcctgtg acctggttat ctgttgtcaa cccctaccgt 4800
gggccagcca ccccactctg gctccactgt ctcttccctg actccccagc cactctagag 4860
tcaggcgagg tggagcctcc tctcccctgc aacgtaggat cgaaccctgg gttcgatccc 4920
gtggagatgg gaacggcaac ccactccagt attcttgtct ggagaatccc atggacagaa 4980
gagcctggga ggctacagtc catagggttg cagagttgga catgactgaa gcgacttagc 5040
atgcacccag tcaccccagc cagagaggcc aaggggagac gcctcacctc ccagagctca 5100
acagcaggct gggcacagca cagctgcagg tttgacttct gcctcctaca ggcatcaacc 5160
cagcttccat tcgggggacg aacaccggtg tctgggtggg tgtgagtggc tctgaggctt 5220
cagaggctct gagccgagac cctgagaccc tcgtgggcta cagcatggtg ggctgccagc 5280
gtgccatgtt ggccaaccgc ctctccttct tctttgactt caaaggtggg tgcccacaca 5340
gcccttttgt ttctgactcg ggcctggggt ggggggaggc ggcaggggcc ggatgacagc 5400
tgagaccctt ccagactctg accacacctc ccctaggaag gccagcagga acaaggtcct 5460
ggtggtgtgg gttccacgtg gagagcactc agtagagctg tcagagcccc aaggtatagg 5520
gtggggaggc ggtcccacgg ctgcattgtg tccttgcctg cagggcccag catcaccctg 5580
gacacggcat gctcctccag cctgctggcc ctgcagaggg cctaccaggc catccagaga 5640
ggggagtgcg ccatggccat tgtcggcggc gtgaacatcc ggctgaagcc caacacctcg 5700
gtgcagttca tgaagctggg catgcttagc cccgagggca cctgcaagtt tttcgatgca 5760
tcaggtgaga gcagtgggca tggggccccg ggaagtgcct ccaccctcga ttctatccgg 5820
cacaagcccc tgagcccttc cctgagctca tgagcctgaa gtgccctccg cccccaggga 5880
atggctactg ccgtgcaaag gctgtaatgg ccatccttct gaccaagaag tccctggccc 5940
gacgggtgta cgccaccatc ctcaacgctg gcaccaacac ggatggctgc aaagagaaag 6000
gtggaagctg gcctggggca ggcgagggtg gggctacggg tagtcgggcg gggctggggg 6060
tgctgaggcc tggacccgcc cccaggcgtc accttcccct ccggagaggc acaggagcag 6120
ctcatcagct ccctgtataa gccggccggg ctggacccgg agaccctgga gtacgttgaa 6180
gcccatggca ccggtaccaa ggtgagaccc ctgcctggcc ctgctcatat cccacgtccc 6240
acgccagaga agcaccaggg cggggtcctg acctccctga gttccccata ggtgggcgac 6300
ccccaggagc taaacggcat cgtgcaagcc ctgtgtggca cccgccagag cccccctgcgg 6360
attgggtcca ccaagtcgaa catgggacat ccggagcccg cctcagggct cgcggcgctg 6420
gccaaggtag gcaggcgagt ctagggccat cttgtccctg ccccgtcagc gtcttatagc 6480
ctgctggggg aagggtccct tccggctgtt ctgtgggata tgggtcatac tgaggcccgg 6540
agagcaggcc gccagcatgt ggccagcccc tgcctggttt cacagggcca gacattttac 6600
ccaagcactt gttccccaag gggccagcca gagggagcag aagcaacagg gcagcccgtg 6660
tttccaggct cgctctccct gtggcctcct gaccagctgg tagcttggag gacccaggtc 6720
actactggtt gagcttctga gtatgatggg agcttcctgg tggtctcagc tccctgggcc 6780
accatagcca cctgtctgca gctcttagct tgggagatgg ggtggggaat ggctgaggag 6840
cctttgtcta gatccacagc caatgaggct gggaggtggc agggccccag gtgaggccta 6900
gggctgagag gagacagagc atgtggcttg gtcaccaaga ccgctgcatt ggggcaggga 6960
cgagctttgg gggagaatga aattgcttgc agcgggcaag ggcttctggg gtgacacaga 7020
gggtccttag gaggggatgt acctgaagcc catcccgacc agcaggggca gggagcccag 7080
ggccggccgt cttgttgacc gcgaggcacc cacaggtgct gctgtccctg gagcacgggc 7140
tctgggcccc caacctgcac ttccacaacc caaaccccaa gatcccagca ctgcaggatg 7200
ggcggctgca ggtggtggac cggcccctgc ccgtcctcgg gggcaacgtg ggcatcaact 7260
cctttggctt cggtggctcc aacgtgcacg tcatcctcca gcccaactcc cagccactgc 7320
caccgcctgc cccacatgcc gccctgcccc gtctgctgcg ggccagtggg cgcaccctgg 7380
agggtgtgca gggtctgctg gagctaggcc tccagcacag ccagaacctg gccttcgtga 7440
gcatgctcaa tgacatcgcg accccctccc cagcagccat gcccttccgt ggctacgccg 7500

```
tgctgggcag ccagggggc agccagaagg tgcagcaggt gctggccggc aagcgcccac   7560
tctggttcat ctgctccggt gagccccgac ccacccgccc cacctcaggt catccccgag   7620
gcccgcatgg gctgggactg cacggcgctg ccctgacatc tccctccggg acaggtatgg   7680
gcacacagtg gcgcgggatg gggctgagtc tgatgcgtct gagccgcttc cgcgactcca   7740
tcctgcgctc ggatgaggcc gtgaagcctc tgggactgca ggtgtcacag ctgttgttga   7800
gcacagacga ggccatcttt gatgacatgg tcatctcctt cgtgagcctc actgccatcc   7860
aggtgtgccc ctggggtctg ggtgagccg gctggcaggg tggtgagcct ggggtccccg   7920
agactggcat gacccatcct gttcccaccc cacccccaga tcgcgctcat agacctgctg   7980
acctccatgg gccttcagcc cgacggcata atcgggcact ccctgggtga ggtggcctgt   8040
ggctatgccg acggctgcat ctctcaggag gaggccatcc tctctgccta ctggagaggc   8100
cagtgcatca aggaggccaa catcccgccc ggggccatgg cggctgtagg taggcactgc   8160
cctctgctcc cctgtcgcgc tccacccctg ggcctgaggg tctccatagg aggtggtcat   8220
ctgtactggc acctttctgt gttggcgctg ggcagaggcc agggcctggg ggcagctcac   8280
cagccactgt cctcaccgca gggtgagaac aaccctgaca gcctgccccg ctatgccccg   8340
gatggccttg gagcccggca tacttgccca tgggtgtcag tagaggccag cgtgattttc   8400
acatgaaccc atggggggga tgctgcagac ggagtgggcc tgctctcact tgggacaggc   8460
atcggaagga cgcaggagac cacaaaagga cgtgaaaggg gctgttggga gagtgaggcc   8520
aaagccctct ctggtaggcc aggcgtggga cccgaaactg gctccacctg taggacggta   8580
ttaatgacac cttcgtctga gaccagacaa cggcagggat gaaactgcct cgtaaaggtg   8640
ccgctcggca gcttgtcatt agggccaccc gggcagcatt ccccttcctg gggagggctg   8700
tgtgggggtg cctgctcccc atgccaccct ttgaggctct cttctgctcc caggcttgac   8760
ctgggaggag tgtaagcagc gctgcccccc tggcatcgtg cctgcctgcc acaactgcat   8820
cgacaccgtg accatctcgg gacctcaggt gggccctggg aggcaaggcc tcgtccccaa   8880
gtcccctttc acccccgcag agcgtgctct gcgcggggag cccggcactg gcccggaccc   8940
ggactgccgt cagcgccccc gtccctcccc gtctgcgctc cccccaggcc tccatgttgg   9000
agttcgtgca gcagctgaag caggagggcg tgttcgccaa ggaggtgcgg acgggcggca   9060
tggcgttcca ctcctacttc atggacgcta tcgcccccat gctgcttcag cagctcaaga   9120
aggtgggtgg ctgtccccgc gctgtgtggc gggggccctc cctgaggaca ggcggggaag   9180
gcaggcccca gcttcctnag ctgacccgcc ggccttcgct aggtgatccg ggagccccag   9240
ccgcgttccc cacgctggct cagcacttcc atccccgaga cccagtggca ggagagcctg   9300
gcccgcacct tctcggccga gtacaacgtg aacaacctgg tgagccccgt gctgttccag   9360
gaggcgctgt ggcgcgtgcc cgaggacgcc gtggtgctgg agatcgcacc ccatgcactg   9420
ctgcaggtac gcgtagtcct gcagggccgg cgggctggcc gggcgcgggg ggctgagcgg   9480
ggggccagtg ggaactgacc agggggaggc ccagcccgcc tctgcctctg caggccgtcc   9540
tgaagagagg cctcaagtcc agctgcacca tcatccccct gatgaagaag gaccacaggg   9600
acaacctaga gttcttcctc agcaacgtgg gccagctcta cctgaccggg tgcggccgct   9660
ctccctgctc aaccctggga ggctcctccc cagccaggcc accgggcggc cttgagatgg   9720
tccccaggaa gcagacctct gggtgctggg ccactttcca caccccttggc atgcccccca   9780
ccccaccctg tctcaggcgt ctccaaggtc tttaggggag atgggttgac cgtgggtcaa   9840
gcagtgggtg ttgcagggca ttcacaaagc tccctttttgc accctccagc attgacgtca   9900
```

```
accccaacgg gctgttccca cctgtggagt tcccagctcc ccggggcacc cccctcattt   9960
ccccccacat caagtgggac cacagccaga cctgggatgt gcccactgct gaggacttcc  10020
ccagtggctc cagtagctct tctgccacca tctataagat cggtgagtcc ttgcaatgca  10080
ggcgggcagg ggggcggggt ggcttcctcc acagcggtgg cactaaggcc caggccccac  10140
agacatcaac cccgagtccc ctgaccacta tctggtggat cactgcatcg acggtcgcat  10200
catcttcccg ggcactggct acctgtgcct ggtctggaag acactggccc gagccctgga  10260
ccagaacatg gagcacacgc ctgtagtatt cgaggacgtg acgctgcacc aggctgtcat  10320
cctgccgaag acaggtgagg aaggtggctc aagctatggg gtgggagggc cagctgccga  10380
cccctgcagc tgacctctgc ccctgctgcc cacagggatt gtgctcctga aagtgcggct  10440
tctggaagct tcctgtacct ttgaggtgtc tgagaatggc aacctgatcg cgagcggtga  10500
gcaggggccc tggaccgggc tgcagggtcc ctgctggggg tctctgggta gaccttagct  10560
accggcttag ccctgccctc actcaggccc ttctgccatc cctgcccaca gggaaggtat  10620
accagtggga agatcccaac cccaagctct ttgacaaccg gtatggcccg gaccctgcga  10680
cccccgtgga ccccacaact gccatccacc tgtcccgtgg tgatgtatac aaggagctgc  10740
agctgcaggg cttcaactac ggcccctact tccaaggtat ccttgaggcc agctccgaag  10800
gtacgtacaa gggaggtccc actttgtgtt ttggggccaa cccctgctgc ctggtgtgag  10860
ggggccacga ggggtccccc caggttgggg cacacagagg agagggccca cggcaggaag  10920
agacctagcc tggccaaaac gacagcccct ttctccccag gcaacacagg ccagctgctc  10980
tggaaggaca actgggtgac cttcatggac accatgctgc agatgtctat cctggccccg  11040
agcaagcgca gcctgcgcct gcccacacgc atcaccgcca tctacatcca cccggctacc  11100
caccagcaga agctgtacac gctgcaggac aagacacaag gtcagccctg ccctggcccc  11160
acacacgtgc ctccccgttc ctaggccctg cccaccctca cccagcgtgt ccccacagtg  11220
gccgacgtgg taataaacag gtgtctggac accacggtgg ctggcggcat ctacatctca  11280
aggatccaca cctcggtggc cccccggcat cagcaggagc agctggtgcc catcctggag  11340
aagttctgct tcacaccgca cgtggagact gggtgcctgg ctgggaacct ggccctgcag  11400
gaggagctgc aactgtgtgt gggtgagtct tttgcaccca ccaccctcat cccggggccc  11460
agcttccagt tcccgggccc cgttatccca tcatagcctc tcctacgtgt ggggtctacc  11520
tctgccttcc ttgtgagtgc ccctggcttc ccctacctgg agctgatttc ttcagagggg  11580
gcctttggca gaaaaggtga cagattttcg cccttcttgt cttgtaccac cagccagttg  11640
cacaggcatt agaccacctt ttacccaggg ctcatgccca antgaggggt cgggatggtg  11700
ggggagctgg gaagggcagc caggccggca aagcatggaa cccatcctct ggggaaccca  11760
tactctgggg ctcacacctg catgggggca gggctgccct ttgcccacct agtgtaccaa  11820
tggtcagtgc cagtttccag ccctggagga ctggacagtc cactccatcc ctctatcttc  11880
cgtcagtggg cagaaccagg tagtgggttc tgcttcaagc agtcactagt tcctggtcgg  11940
gggagcttca ggaaccccag cccagctgag gctcttccct gacatgtgac tctcccctcc  12000
ccagggctgg cacaggcact gcagaccagg gtggcccagc aggggataaa gatggtggtt  12060
cctgggctgg atggtgccca ggctccccag gaggccccac agcaaggcct gcctcggctg  12120
ctggccaccg cctgccagct gcaactcaac gggaacttac agatggagat gggccagatc  12180
ctagcccagg agagagccct gctgtgtgat gacccccttgc tcagtgggct cctcaactcc  12240
ccagcactca aggcgtgcgt gacacttgcc ctggagaaca tgaccagcct caagatgaag  12300
```

gtggtgaggt gggcgtcccg cgcggccgca ggcccagtgc tcaaggactc agatatcggc 12360
agtcccgaac ctaagggagg gctggggcct ctcagacgtg aggtcgccca actcaagatg 12420
gagctgagac tgcccagaca ccgaagggga agggggcact gaagggactg gttccagggg 12480
tgtggtgggc agggcagcac tggccaatga cctctgcaga atcggtgggt gggcctttct 12540
gggaaacacc cagctgaggt gggggaacgc ctgcccaggg gcagctgatc caagaagcct 12600
attccatccc aggtgctagc tggtgacggc caactgtatt cccgcatccc cacgctgctc 12660
aacacccagc ccctgctgga gctggactac acagccactg accgccaccc ccaggccctg 12720
gaggctgccc aggccaaatt gcagcagctc gatataaccc agggccagtg ggacccctcg 12780
gacccggccc ccagcaacct gggtggggcc aacctcgtgg tgtgcaacta tgccttagcc 12840
agcctcggtg acccggccac ggctgtcggt aatatggtgg ctgccctcaa ggagggaggc 12900
ttcctgttgc tgcacacgct gctcagagga caccccttgg gagagactgt caccttcctc 12960
acttgccctg agccacaaca aggccaacgg cacctcctga gccaggtaca ggcggagccg 13020
ggattgggtg gatggggctg ggggggcggg accgggaggc tgcagagccc tgaccccctc 13080
aactcacagg atgagtggga gcgcctgttt gctggtgcgt ccctgcacct ggtggccctg 13140
aagaagtcct tctacggctc ggtgctcttc ctgtgccgcc ggctggcccc gcttgacagc 13200
ccaatcttcc tgcctgtgga ggacaccagc ttccagtggg ttgactccct gaaggtcagt 13260
ccttcccagc ccctaccagg ccaaggctga cccggcttcc agtgtcggga cctgggggaa 13320
ttcccccccca tcaggcaacc cttcccattg gtcaaccctt ccttacatcc ttctacagaa 13380
catcctggcc gattcctcct cccgggccgt atggctcatg gctgttggct gcaccacctc 13440
aggggtcgtg ggcttggtga actgtctccg gaaagagcct gacgggcacc ggattcggtg 13500
agatgcccac tgcgctacgt gcccccttgcc cccgggaccc aaccacagcc tcccctcacc 13560
tgtctggctg cccacaggtg cgtcctggtg tctaacctca acagcacgtc ccccatccct 13620
gagacagacc cgaagtcctt ggagctgcag aaggtgctcc agagtgacct ggtgatgaat 13680
gtctaccgtg atggggcctg gggagcgttc cgccacttcc cactggaaca aggtgagccc 13740
cccgggactg ccctgctcct ccgggttcct cgcctcccag ctgggtggac tgaggagagg 13800
gcaagaggac tctggctgga agccctgctc caggccaggg ccacatgcga tcctaggggc 13860
tccactttct gtcacccccct agacaagccc gaggagcaga cagagcatgc cttcataaat 13920
gtcctcaccc gaggggacct gtcttccatc cgctgggtct gctcccctct gcgccacagc 13980
cagcccacgg cccctggctt ccagctctgc accatctatt atgcctccct caacttcaaa 14040
agaaatcatg ctggccacgg gcaagctgtc ccccgacgcc atcccaggta caggcagccc 14100
acggtagggg gaccagaaca aagacccccc ccaccccggg gccggggcct gggacgagaa 14160
gggtcctcac ccaacagtgc tcaggaacct gggaggctcc tcccagtgag gtcaggggct 14220
cactcacccg ccatctgccc ccaggaattg ggcctctcgg aactgcctgc taggcatgga 14280
gttctctggc cgagatgcca gcgggaagcg tgtgatgggg ctggtacccg ccgaaggcct 14340
ggccacctcc actctggtgc ctcagagctt cctgtgggac gtgccttcca actggtgagt 14400
caccagggct gggacctggg gcccgacatg gacgtggctg ggcatcaggc cagagctgac 14460
ccctgcactg tgcccttagg accctggagg aggccgcctc ggtgcccgtt gtctacagca 14520
cagcctacta cgcgctgatg gtccgcgggc gcatgcagcc aggcgagacg gtgctcattc 14580
actcgggctc cggcggcgta ggccaggctg ccatcgccat cgccctcagc ctgggctgcc 14640
gtgttttccc acttgtgggt aagcctccaa cccttcccag agcccaggat tgtctgcctg 14700

```
gcagcactgc taaagcccaa actcaccagg tgtgcctctc tctgccaggg tcagccgaaa  14760
agcgggcata cctccagtcc aggttccccc agctcaacga aaccagcttt gccaactccc  14820
gggacacatc ctttgagcag catgtgctgt ggcacacagc cgggaagggt gagtggtccc  14880
catcactcac cacccaccat ccgcctgtat cctcagcccc ctcctcctcc catcccccac  14940
tcaccagcca agctggagga gacgctggcc catgctggga cagggtctag accttcagac  15000
tcatgtcagg ttggccgggc tgtgaccttc actatgggga cccggcttgc cccccatccc  15060
aaggtgctga cctggtcctc aactccctgg cggaagagaa gcttcaggcc agtgtgcggt  15120
gcctggccca gcacggtcga ttcctggaaa ttggcaaatt tgacctttcc aaaaaccacc  15180
ccctgggtga gatggggcgg caggcctggt gggtggctgg gtgggcaggg ggctgttggg  15240
cagagtgggg gtctgcaggg tggtaggctg tgggctatgt ggtgaggggc cccccgcctg  15300
cccacctgtc caggcatggc catcttcctg aagaacgtga ctttccacgg gatcctactg  15360
gactctctct ttgaagaaaa caacaccatg tggcaggaag tgtcgacact gctgaaggcg  15420
ggcatccgga agggtgtggt gcagcccctc aagcgaacag tgttccccag gacccaggcg  15480
gaggacgctt tccgttacat ggcccagggc aaacacatcg gcaaagtggt cattcaggtg  15540
agtggggggc cctgggggtc tctggcccca gccctggccc ctgcagcagt gcgtgaacag  15600
gggccctgct tgggctgcag gtacgtgagg aagagcagga ggcggtgctg cacgggacca  15660
aacccaccca gatggtggcc ttgtgcaaga ccttctgccc agcccacaag agctacatca  15720
tcactggggg cctgggtggc tttggcctag agctggccca ctggctcgtg gagcgagggg  15780
cccagaagct ggtgctgacc tcccgctctg ggatccgcac aggtgaattg cccgacggtt  15840
gtgcattggg caagaacctt cttcaaaacc ctttatggtg ctttaagggc accttaggct  15900
tgggaccaga ccttaatttg ccaatcctct ctcactgtct gtcccacagg ctaccaagcc  15960
aggcaggtcc acgagtggag acgccagggt gtgcaggtcc tggtgtccac cagcgacgtc  16020
agcrcactgg atggcaccyg gagccttatc actgaggccg cccagcttgg gcccgtggga  16080
ggcatcttca acctggccgt ggtgaggacg gctttagagg ggctggagcc agctgcccag  16140
ggaagggccc ctcctaagaa gccctccaaa ggcctggggc cgaggcaggt gctaagatcc  16200
cctcacccca ggtcctgaga gatgccatgc tggataacca gacccctgag ttcttccagg  16260
acgtcaacaa gcccaagtac aatggcaccc tgaacttgga caggtgggct cctcccttct  16320
cctctcccgc cttctccctg cacagccctt gcactggtgt ccagagacct ggccatgggc  16380
ctccgctggg gtctgaccac aggtccaggg aaggggaggc ggtttggcgg gtaagcagga  16440
gtcctgggca tgacagccgg ggggctgggg aatccggctg ggggtgactt aagaacccac  16500
agggtgaccc gggaggcatg cccagagctg gactacttcg aggtcttctc ctccgtgagc  16560
tgcgggcgtg gcaatgccgg ccagaccaac tacgggttcg ccaactccac catggagcgc  16620
atatgtgaga agcgtcggca cgacggcctc ccaggtgggc ccacctgcca ctccccgatt  16680
ggtgcggtcc caccctcata actaccccga ctcaccacag cgccactgcc cacccacagg  16740
cctcgccgtg cagtggggtg cgattgctga cgtgggcctc ctcatggagc tgaagggcac  16800
taaagacaaa gccatcggcg ggacgctgcc ccagcgcatc acctcctgca tggaggttct  16860
agacctcttc ctgaaccagc cccaccccgt cctgagcagc tttgtgttgg cagagaaggc  16920
tacatcccgt ggccccagcg gcagccacca ggacctcgtg aaggctgtga ctcacatcct  16980
gggtgaggca agcacccttg ccccccttgc caccggtaga cactcgtctt ccgagtctgg  17040
tctcccaggc tgcaaagggg ggcgtgctgg gcttgctcat ggagggagag gcataggtgg  17100
```

```
tctgtgcaaa tttgggtggg ggctgtgggt cccatggtac catctgttca gttcagtcgc  17160
tcagtcttgt ccgactcttt gcgaccccgt gaatcgcagc atgccaggcc tccctgtccg  17220
tcaccaactc ctggagttta ctcaaactca tgtccagggt acaataccca cccaggaccc  17280
ctcccgcgtt gccaactgag ctgcctgcgc caccccccag gcatccgtga cttggccacc  17340
gtcaacctgg acagctcgct ttcagacctt ggcctcgact cactcatggg cgtggaggtg  17400
cgccagatgc tggagcgtga gcacaacctg ctgctgtcca tgcgggaaat ccggcagctc  17460
acaatccaca agctgcagga gatttccgcg caggctggca cagctgatgg taggtatgga  17520
gggggtgtcc ccaaagcagc actgtcccct cagggctctt ggcctccgaa caggtcaggg  17580
cttgtccatc tggccccttc ctgagaggcc tccttgggcg cccagcgccc cccacccatc  17640
tgccctggcc acccgtggcc gacgggtgtg catgtctgtg tgtttgtggc aggggaccct  17700
atggtatcat ccctggtatc tgcccctctt cacagagctg acggactcca cacccaaatt  17760
cggcagccct gcccaatcgc acacccagct gaacctgagc accctgctgg tgaaccccga  17820
gggcccgacc ttgacacggc tcaactcggt gcagagctcc gagcggcccc tgttcctggt  17880
gcaccccatc gagggctcca ccaccgtgtt ccacagcctg gccaccaagc tcagcatccc  17940
cacctatggc ctacagtgta caggaggtat gtcaggggcc tacggggctt gcccccaagg  18000
gagttgggga tggcaaggca cctgcagaca agggctaaac ctcatgctgt gcccgcagcg  18060
gcacccctgg acagcatcca gagcctggcc acctactaca tcgagtgcat caggcaagtg  18120
cagccagagg ggaactaccg catcgctggc tactcctacg gggcctgcgt ggctttcgag  18180
atgtgctcac agctgcaggc ccagcagaac gctggcccca cgaacaacag cctcttcctg  18240
tttgacggct cgcacacctt cgtgatggcc tacactcagg tgagggcggc agcggacggg  18300
agtccgcagg cccagcccct tgtacctgcc actgcaacag ctcttcctcc ctttgcagag  18360
ctaccgggcc aagctgaacc ccggctgcga ggcagaggcc gaggccgagg ccatgtgctt  18420
cttcatgcag cagttcacgg aggcggagca tagtagagtc gacccggcgt ggggcccggc  18480
ctcccgatgc ccccgccccc gcccccggcg ctgctcgctc actgtcctgt cctacaggtg  18540
ctggaggccc tcctgcccct cggggatctg gaggcgcgtg tggcagccac cgtcgagctg  18600
atcgtgcaga gccacgcggg cctggaccgg cacgcgctca gctttgctgc gcgttccttc  18660
taccacaagc tgcgcgccgc ggaggagtac acgccgcggg ctacctacca cggcaacgtg  18720
acgctgctgc gcgccaagat gggcagcgcc taccaggagg gcctgggcgc cgactacaat  18780
ctgtcccagg tgtgcgacgg caaggtgtct gtacacatca tcgagggcga ccaccgcacg  18840
ctgctggagg gcagcggcct ggagtccatc cttagtatta ttcacagctc cctggccgag  18900
ccgcgcgtca gcgtgcggga gggctaggcc accggcccgc cccccgcctc ccacctgccg  18960
accctggcac cgcaccccgc gtgcaggcgc ccataggacc agcaccccca cgcacacgca  19020
cacagcccac cccgcggctt ccctgggcgc agggccgaga cccgcgccgc cgactcggag  19080
acctgcctgg tctgtgaaga gtcggctgag ccactagccg ggccgagctt ccagaaccgc  19140
acgggctctg ctgcactggt gtggtgttcg gttttctggt tggattctcc tatttattgc  19200
gtcgccatgg ggggcggagg gtggcgaggg gagacgctgg tcggtccacc tgtgaagctg  19260
gcgcacgcgg gagccgggcc cagggcccca tgatgccgga ggtcgcgcgg agcagccctg  19320
ggcgctgggc acccacccta tttgtctgtg ttcgtttttc aagaaataag gttcaaattg  19380
ctgcgtgggt tttgaaattt actgtaattg tctgtgtaaa gaaccgtgtc tgtactctgt  19440
ttcatttttc acgaacctgg taaagatgtt gtctcccatg attaaatctc tccttcgctc  19500
```

```
tggcgtctgg gcatcctttc atcctgcctg ctgatcagct ctgtgagcct ccactgtcct  19560

ggcgccccag ggagtaccac cctctgcttc ccgcaggagt gtgtgtgtgt ggaggggtga  19620

tacctggctc cagaaaacag gctggacacc tccagggaag gggccctcga tcaaggaaac  19680

ttgaccagga ggggacaggt aggcagtctg atgatgggct ggcataattg aggaccccccc  19740

cacctagggt agccttgcca                                              19760


<210> SEQ ID NO 2
<211> LENGTH: 2513
<212> TYPE: PRT
<213> ORGANISM: Bos taurus

<400> SEQUENCE: 2

Met Glu Glu Val Val Ile Thr Gly Met Ser Gly Lys Leu Pro Glu Ser
1               5                   10                  15

Glu Asn Leu Glu Glu Phe Trp Ala Asn Leu Ile Gly Gly Val Asp Met
            20                  25                  30

Val Thr Asp Asp Asp Arg Arg Trp Lys Ala Gly Leu Tyr Gly Leu Pro
        35                  40                  45

Arg Arg Ser Gly Lys Leu Lys Asp Leu Ser Arg Phe Asp Ala Ser Phe
    50                  55                  60

Phe Gly Val His Pro Lys Gln Ala His Asn Met Asp Pro Gln Leu Arg
65                  70                  75                  80

Leu Leu Leu Glu Val Thr Tyr Glu Ala Ile Val Asp Ala Gly Ile Asn
                85                  90                  95

Pro Ala Ser Ile Arg Gly Thr Asn Thr Gly Val Trp Val Gly Val Ser
            100                 105                 110

Gly Ser Glu Ala Ser Glu Ala Leu Ser Arg Asp Pro Glu Thr Leu Val
        115                 120                 125

Gly Tyr Ser Met Val Gly Cys Gln Arg Ala Met Leu Ala Asn Arg Leu
    130                 135                 140

Ser Phe Phe Phe Asp Phe Lys Gly Pro Ser Ile Thr Leu Asp Thr Ala
145                 150                 155                 160

Cys Ser Ser Ser Leu Leu Ala Leu Gln Arg Ala Tyr Gln Ala Ile Gln
                165                 170                 175

Arg Gly Glu Cys Ala Met Ala Ile Val Gly Gly Val Asn Ile Arg Leu
            180                 185                 190

Lys Pro Asn Thr Ser Val Gln Phe Met Lys Leu Gly Met Leu Ser Pro
        195                 200                 205

Glu Gly Thr Cys Lys Phe Phe Asp Ala Ser Gly Asn Gly Tyr Cys Arg
    210                 215                 220

Ala Lys Ala Val Met Ala Ile Leu Leu Thr Lys Lys Ser Leu Ala Arg
225                 230                 235                 240

Arg Val Tyr Ala Thr Ile Leu Asn Ala Gly Thr Asn Thr Asp Gly Cys
                245                 250                 255

Lys Glu Lys Gly Val Thr Phe Pro Ser Gly Glu Ala Gln Glu Gln Leu
            260                 265                 270

Ile Ser Ser Leu Tyr Lys Pro Ala Gly Leu Asp Pro Glu Thr Leu Glu
        275                 280                 285

Tyr Val Glu Ala His Gly Thr Gly Thr Lys Val Gly Asp Pro Gln Glu
    290                 295                 300

Leu Asn Gly Ile Val Gln Ala Leu Cys Gly Thr Arg Gln Ser Pro Leu
305                 310                 315                 320

Arg Ile Gly Ser Thr Lys Ser Asn Met Gly His Pro Glu Pro Ala Ser
```

```
                325                 330                 335

Gly Leu Ala Ala Leu Ala Lys Val Leu Leu Ser Leu Glu His Gly Leu
            340                 345                 350

Trp Ala Pro Asn Leu His Phe His Asn Pro Asn Pro Lys Ile Pro Ala
        355                 360                 365

Leu Gln Asp Gly Arg Leu Gln Val Val Asp Arg Pro Leu Pro Val Leu
    370                 375                 380

Gly Gly Asn Val Gly Ile Asn Ser Phe Gly Phe Gly Gly Ser Asn Val
385                 390                 395                 400

His Val Ile Leu Gln Pro Asn Ser Gln Pro Leu Pro Pro Pro Ala Pro
                405                 410                 415

His Ala Ala Leu Pro Arg Leu Leu Arg Ala Ser Gly Arg Thr Leu Glu
            420                 425                 430

Gly Val Gln Gly Leu Leu Glu Leu Gly Leu Gln His Ser Gln Asn Leu
        435                 440                 445

Ala Phe Val Ser Met Leu Asn Asp Ile Ala Thr Pro Ser Pro Ala Ala
    450                 455                 460

Met Pro Phe Arg Gly Tyr Ala Val Leu Gly Ser Gln Gly Gly Ser Gln
465                 470                 475                 480

Lys Val Gln Gln Val Leu Ala Gly Lys Arg Pro Leu Trp Phe Ile Cys
                485                 490                 495

Ser Gly Met Gly Thr Gln Trp Arg Gly Met Gly Leu Ser Leu Met Arg
            500                 505                 510

Leu Ser Arg Phe Arg Asp Ser Ile Leu Arg Ser Asp Glu Ala Val Lys
        515                 520                 525

Pro Leu Gly Leu Gln Val Ser Gln Leu Leu Leu Ser Thr Asp Glu Ala
    530                 535                 540

Ile Phe Asp Asp Met Val Ile Ser Phe Val Ser Leu Thr Ala Ile Gln
545                 550                 555                 560

Ile Ala Leu Ile Asp Leu Leu Thr Ser Met Gly Leu Gln Pro Asp Gly
                565                 570                 575

Ile Ile Gly His Ser Leu Gly Glu Val Ala Cys Gly Tyr Ala Asp Gly
            580                 585                 590

Cys Ile Ser Gln Glu Glu Ala Ile Leu Ser Ala Tyr Trp Arg Gly Gln
        595                 600                 605

Cys Ile Lys Glu Ala Asn Ile Pro Pro Gly Ala Met Ala Ala Val Gly
    610                 615                 620

Leu Thr Trp Glu Glu Cys Lys Gln Arg Cys Pro Pro Gly Ile Val Pro
625                 630                 635                 640

Ala Cys His Asn Cys Ile Asp Thr Val Thr Ile Ser Gly Pro Gln Ala
                645                 650                 655

Ser Met Leu Glu Phe Val Gln Gln Leu Lys Gln Glu Gly Val Phe Ala
            660                 665                 670

Lys Glu Val Arg Thr Gly Gly Met Ala Phe His Ser Tyr Phe Met Asp
        675                 680                 685

Ala Ile Ala Pro Met Leu Leu Gln Gln Leu Lys Lys Val Ile Arg Glu
    690                 695                 700

Pro Gln Pro Arg Ser Pro Arg Trp Leu Ser Thr Ser Ile Pro Glu Thr
705                 710                 715                 720

Gln Trp Gln Glu Ser Leu Ala Arg Thr Phe Ser Ala Glu Tyr Asn Val
                725                 730                 735

Asn Asn Leu Val Ser Pro Val Leu Phe Gln Glu Ala Leu Trp Arg Val
            740                 745                 750
```

```
Pro Glu Asp Ala Val Val Leu Glu Ile Ala Pro His Ala Leu Leu Gln
        755                 760                 765

Ala Val Leu Lys Arg Gly Leu Lys Ser Ser Cys Thr Ile Ile Pro Leu
    770                 775                 780

Met Lys Lys Asp His Arg Asp Asn Leu Glu Phe Phe Leu Ser Asn Val
785                 790                 795                 800

Gly Gln Leu Tyr Leu Thr Gly Ile Asp Val Asn Pro Asn Gly Leu Phe
                805                 810                 815

Pro Pro Val Glu Phe Pro Ala Pro Arg Gly Thr Pro Leu Ile Ser Pro
            820                 825                 830

His Ile Lys Trp Asp His Ser Gln Thr Trp Asp Val Pro Thr Ala Glu
        835                 840                 845

Asp Phe Pro Ser Gly Ser Ser Ser Ser Ser Ala Thr Ile Tyr Lys Ile
    850                 855                 860

Asp Ile Asn Pro Glu Ser Pro Asp His Tyr Leu Val Asp His Cys Ile
865                 870                 875                 880

Asp Gly Arg Ile Ile Phe Pro Gly Thr Gly Tyr Leu Cys Leu Val Trp
                885                 890                 895

Lys Thr Leu Ala Arg Ala Leu Asp Gln Asn Met Glu His Thr Pro Val
            900                 905                 910

Val Phe Glu Asp Val Thr Leu His Gln Ala Val Ile Leu Pro Lys Thr
        915                 920                 925

Gly Ile Val Leu Leu Lys Val Arg Leu Leu Glu Ala Ser Cys Thr Phe
    930                 935                 940

Glu Val Ser Glu Asn Gly Asn Leu Ile Ala Ser Gly Lys Val Tyr Gln
945                 950                 955                 960

Trp Glu Asp Pro Asn Pro Lys Leu Phe Asp Asn Arg Tyr Gly Pro Asp
                965                 970                 975

Pro Ala Thr Pro Val Asp Pro Thr Thr Ala Ile His Leu Ser Arg Gly
            980                 985                 990

Asp Val Tyr Lys Glu Leu Gln Leu  Gln Gly Phe Asn Tyr  Gly Pro Tyr
        995                 1000                1005

Phe Gln  Gly Ile Leu Glu Ala  Ser Ser Glu Gly Asn  Thr Gly Gln
    1010                1015                1020

Leu Leu  Trp Lys Asp Asn Trp  Val Thr Phe Met Asp  Thr Met Leu
    1025                1030                1035

Gln Met  Ser Ile Leu Ala Pro  Ser Lys Arg Ser Leu  Arg Leu Pro
    1040                1045                1050

Thr Arg  Ile Thr Ala Ile Tyr  Ile His Pro Ala Thr  His Gln Gln
    1055                1060                1065

Lys Leu  Tyr Thr Leu Gln Asp  Lys Thr Gln Val Ala  Asp Val Val
    1070                1075                1080

Ile Asn  Arg Cys Leu Asp Thr  Thr Val Ala Gly Gly  Ile Tyr Ile
    1085                1090                1095

Ser Arg  Ile His Thr Ser Val  Ala Pro Arg His Gln  Gln Glu Gln
    1100                1105                1110

Leu Val  Pro Ile Leu Glu Lys  Phe Cys Phe Thr Pro  His Val Glu
    1115                1120                1125

Thr Gly  Cys Leu Ala Gly Asn  Leu Ala Leu Gln Glu  Glu Leu Gln
    1130                1135                1140

Leu Cys  Val Gly Leu Ala Gln  Ala Leu Gln Thr Arg  Val Ala Gln
    1145                1150                1155

Gln Gly  Ile Lys Met Val Val  Pro Gly Leu Asp Gly  Ala Gln Ala
    1160                1165                1170
```

```
Pro Gln  Glu Ala Pro Gln Gln  Gly Leu Pro Arg Leu  Leu Ala Thr
    1175                 1180                 1185

Ala Cys  Gln Leu Gln Leu Asn  Gly Asn Leu Gln Met  Glu Met Gly
    1190                 1195                 1200

Gln Ile  Leu Ala Gln Glu Arg  Ala Leu Leu Cys Asp  Asp Pro Leu
    1205                 1210                 1215

Leu Ser  Gly Leu Leu Asn Ser  Pro Ala Leu Lys Ala  Cys Val Thr
    1220                 1225                 1230

Leu Ala  Leu Glu Asn Met Thr  Ser Leu Lys Met Lys  Val Val Leu
    1235                 1240                 1245

Ala Gly  Asp Gly Gln Leu Tyr  Ser Arg Ile Pro Thr  Leu Leu Asn
    1250                 1255                 1260

Thr Gln  Pro Leu Leu Glu Leu  Asp Tyr Thr Ala Thr  Asp Arg His
    1265                 1270                 1275

Pro Gln  Ala Leu Glu Ala Ala  Gln Ala Lys Leu Gln  Gln Leu Asp
    1280                 1285                 1290

Ile Thr  Gln Gly Gln Trp Asp  Pro Ser Asp Pro Ala  Pro Ser Asn
    1295                 1300                 1305

Leu Gly  Gly Ala Asn Leu Val  Val Cys Asn Tyr Ala  Leu Ala Ser
    1310                 1315                 1320

Leu Gly  Asp Pro Ala Thr Ala  Val Gly Asn Met Val  Ala Ala Leu
    1325                 1330                 1335

Lys Glu  Gly Gly Phe Leu Leu  Leu His Thr Leu Leu  Arg Gly His
    1340                 1345                 1350

Pro Leu  Gly Glu Thr Val Thr  Phe Leu Thr Cys Pro  Glu Pro Gln
    1355                 1360                 1365

Gln Gly  Gln Arg His Leu Leu  Ser Gln Asp Glu Trp  Glu Arg Leu
    1370                 1375                 1380

Phe Ala  Gly Ala Ser Leu His  Leu Val Ala Leu Lys  Lys Ser Phe
    1385                 1390                 1395

Tyr Gly  Ser Val Leu Phe Leu  Cys Arg Arg Leu Ala  Pro Leu Asp
    1400                 1405                 1410

Ser Pro  Ile Phe Leu Pro Val  Glu Asp Thr Ser Phe  Gln Trp Val
    1415                 1420                 1425

Asp Ser  Leu Lys Asn Ile Leu  Ala Asp Ser Ser Ser  Arg Ala Val
    1430                 1435                 1440

Trp Leu  Met Ala Val Gly Cys  Thr Thr Ser Gly Val  Val Gly Leu
    1445                 1450                 1455

Val Asn  Cys Leu Arg Lys Glu  Pro Asp Gly His Arg  Ile Arg Cys
    1460                 1465                 1470

Val Leu  Val Ser Asn Leu Asn  Ser Thr Ser Pro Ile  Pro Glu Thr
    1475                 1480                 1485

Asp Pro  Lys Ser Leu Glu Leu  Gln Lys Val Leu Gln  Ser Asp Leu
    1490                 1495                 1500

Val Met  Asn Val Tyr Arg Asp  Gly Ala Trp Gly Ala  Phe Arg His
    1505                 1510                 1515

Phe Pro  Leu Glu Gln Asp Lys  Pro Glu Glu Gln Thr  Glu His Ala
    1520                 1525                 1530

Phe Ile  Asn Val Leu Thr Arg  Gly Asp Leu Ser Ser  Ile Arg Trp
    1535                 1540                 1545

Val Cys  Ser Pro Leu Arg His  Ser Gln Pro Thr Ala  Pro Gly Phe
    1550                 1555                 1560

Gln Leu  Cys Thr Ile Tyr Tyr  Ala Ser Leu Asn Phe  Lys Arg Asn
```

```
    1565                1570                1575

His Ala Gly His Gly Gln Ala Val Pro Arg Arg His Pro Arg Asn
    1580                1585                1590

Trp Ala Ser Arg Asn Cys Leu Leu Gly Met Glu Phe Ser Gly Arg
    1595                1600                1605

Asp Ala Ser Gly Lys Arg Val Met Gly Leu Val Pro Ala Glu Gly
    1610                1615                1620

Leu Ala Thr Ser Thr Leu Val Pro Gln Ser Phe Leu Trp Asp Val
    1625                1630                1635

Pro Ser Asn Trp Thr Leu Glu Glu Ala Ala Ser Val Pro Val Val
    1640                1645                1650

Tyr Ser Thr Ala Tyr Tyr Ala Leu Met Val Arg Gly Arg Met Gln
    1655                1660                1665

Pro Gly Glu Thr Val Leu Ile His Ser Gly Ser Gly Gly Val Gly
    1670                1675                1680

Gln Ala Ala Ile Ala Ile Ala Leu Ser Leu Gly Cys Arg Val Phe
    1685                1690                1695

Pro Leu Val Gly Ser Ala Glu Lys Arg Ala Tyr Leu Gln Ser Arg
    1700                1705                1710

Phe Pro Gln Leu Asn Glu Thr Ser Phe Ala Asn Ser Arg Asp Thr
    1715                1720                1725

Ser Phe Glu Gln His Val Leu Trp His Thr Ala Gly Lys Gly Ala
    1730                1735                1740

Asp Leu Val Leu Asn Ser Leu Ala Glu Glu Lys Leu Gln Ala Ser
    1745                1750                1755

Val Arg Cys Leu Ala Gln His Gly Arg Phe Leu Glu Ile Gly Lys
    1760                1765                1770

Phe Asp Leu Ser Lys Asn His Pro Leu Gly Met Ala Ile Phe Leu
    1775                1780                1785

Lys Asn Val Thr Phe His Gly Ile Leu Leu Asp Ser Leu Phe Glu
    1790                1795                1800

Glu Asn Asn Thr Met Trp Gln Glu Val Ser Thr Leu Leu Lys Ala
    1805                1810                1815

Gly Ile Arg Lys Gly Val Val Gln Pro Leu Lys Arg Thr Val Phe
    1820                1825                1830

Pro Arg Thr Gln Ala Glu Asp Ala Phe Arg Tyr Met Ala Gln Gly
    1835                1840                1845

Lys His Ile Gly Lys Val Val Ile Gln Val Arg Glu Glu Glu Gln
    1850                1855                1860

Glu Ala Val Leu His Gly Thr Lys Pro Thr Gln Met Val Ala Leu
    1865                1870                1875

Cys Lys Thr Phe Cys Pro Ala His Lys Ser Tyr Ile Ile Thr Gly
    1880                1885                1890

Gly Leu Gly Gly Phe Gly Leu Glu Leu Ala His Trp Leu Val Glu
    1895                1900                1905

Arg Gly Ala Gln Lys Leu Val Leu Thr Ser Arg Ser Gly Ile Arg
    1910                1915                1920

Thr Gly Tyr Gln Ala Arg Gln Val His Glu Trp Arg Arg Gln Gly
    1925                1930                1935

Val Gln Val Leu Val Ser Thr Ser Asp Val Ser Thr Leu Asp Gly
    1940                1945                1950

Thr Arg Ser Leu Ile Thr Glu Ala Ala Gln Leu Gly Pro Val Gly
    1955                1960                1965
```

-continued

```
Gly Ile  Phe Asn Leu Ala Val  Val Leu Arg Asp Ala  Met Leu Asp
    1970                 1975                 1980

Asn Gln  Thr Pro Glu Phe Phe  Gln Asp Val Asn Lys  Pro Lys Tyr
    1985                 1990                 1995

Asn Gly  Thr Leu Asn Leu Asp  Arg Val Thr Arg Glu  Ala Cys Pro
    2000                 2005                 2010

Glu Leu  Asp Tyr Phe Glu Val  Phe Ser Ser Val Ser  Cys Gly Arg
    2015                 2020                 2025

Gly Asn  Ala Gly Gln Thr Asn  Tyr Gly Phe Ala Asn  Ser Thr Met
    2030                 2035                 2040

Glu Arg  Ile Cys Glu Lys Arg  Arg His Asp Gly Leu  Pro Gly Leu
    2045                 2050                 2055

Ala Val  Gln Trp Gly Ala Ile  Ala Asp Val Gly Leu  Leu Met Glu
    2060                 2065                 2070

Leu Lys  Gly Thr Lys Asp Lys  Ala Ile Gly Gly Thr  Leu Pro Gln
    2075                 2080                 2085

Arg Ile  Thr Ser Cys Met Glu  Val Leu Asp Leu Phe  Leu Asn Gln
    2090                 2095                 2100

Pro His  Pro Val Leu Ser Ser  Phe Val Leu Ala Glu  Lys Ala Thr
    2105                 2110                 2115

Ser Arg  Gly Pro Ser Gly Ser  His Gln Asp Leu Val  Lys Ala Val
    2120                 2125                 2130

Thr His  Ile Leu Gly Ile Arg  Asp Leu Ala Thr Val  Asn Leu Asp
    2135                 2140                 2145

Ser Ser  Leu Ser Asp Leu Gly  Leu Asp Ser Leu Met  Gly Val Glu
    2150                 2155                 2160

Val Arg  Gln Met Leu Glu Arg  Glu His Asn Leu Leu  Leu Ser Met
    2165                 2170                 2175

Arg Glu  Ile Arg Gln Leu Thr  Ile His Lys Leu Gln  Glu Ile Ser
    2180                 2185                 2190

Ala Gln  Ala Gly Thr Ala Asp  Glu Leu Thr Asp Ser  Thr Pro Lys
    2195                 2200                 2205

Phe Gly  Ser Pro Ala Gln Ser  His Thr Gln Leu Asn  Leu Ser Thr
    2210                 2215                 2220

Leu Leu  Val Asn Pro Glu Gly  Pro Thr Leu Thr Arg  Leu Asn Ser
    2225                 2230                 2235

Val Gln  Ser Ser Glu Arg Pro  Leu Phe Leu Val His  Pro Ile Glu
    2240                 2245                 2250

Gly Ser  Thr Thr Val Phe His  Ser Leu Ala Thr Lys  Leu Ser Ile
    2255                 2260                 2265

Pro Thr  Tyr Gly Leu Gln Cys  Thr Gly Ala Ala Pro  Leu Asp Ser
    2270                 2275                 2280

Ile Gln  Ser Leu Ala Thr Tyr  Tyr Ile Glu Cys Ile  Arg Gln Val
    2285                 2290                 2295

Gln Pro  Glu Gly Asn Tyr Arg  Ile Ala Gly Tyr Ser  Tyr Gly Ala
    2300                 2305                 2310

Cys Val  Ala Phe Glu Met Cys  Ser Gln Leu Gln Ala  Gln Gln Asn
    2315                 2320                 2325

Ala Gly  Pro Thr Asn Asn Ser  Leu Phe Leu Phe Asp  Gly Ser His
    2330                 2335                 2340

Thr Phe  Val Met Ala Tyr Thr  Gln Ser Tyr Arg Ala  Lys Leu Asn
    2345                 2350                 2355

Pro Gly  Cys Glu Ala Glu Ala  Glu Ala Glu Ala Met  Cys Phe Phe
    2360                 2365                 2370
```

-continued

```
Met Gln  Gln Phe Thr Glu Ala  Glu His Ser Arg Val  Leu Glu Ala
    2375                 2380                 2385

Leu Leu  Pro Leu Gly Asp Leu  Glu Ala Arg Val Ala  Ala Thr Val
    2390                 2395                 2400

Glu Leu  Ile Val Gln Ser His  Ala Gly Leu Asp Arg  His Ala Leu
    2405                 2410                 2415

Ser Phe  Ala Ala Arg Ser Phe  Tyr His Lys Leu Arg  Ala Ala Glu
    2420                 2425                 2430

Glu Tyr  Thr Pro Arg Ala Thr  Tyr His Gly Asn Val  Thr Leu Leu
    2435                 2440                 2445

Arg Ala  Lys Met Gly Ser Ala  Tyr Gln Glu Gly Leu  Gly Ala Asp
    2450                 2455                 2460

Tyr Asn  Leu Ser Gln Val Cys  Asp Gly Lys Val Ser  Val His Ile
    2465                 2470                 2475

Ile Glu  Gly Asp His Arg Thr  Leu Leu Glu Gly Ser  Gly Leu Glu
    2480                 2485                 2490

Ser Ile  Leu Ser Ile Ile His  Ser Ser Leu Ala Glu  Pro Arg Val
    2495                 2500                 2505

Ser Val  Arg Glu Gly
    2510


<210> SEQ ID NO 3
<211> LENGTH: 19
<212> TYPE: DNA
<213> ORGANISM: Artificial
<220> FEATURE:
<223> OTHER INFORMATION: Oligo nucleotide to act as a forward primer for
      PCR.

<400> SEQUENCE: 3

ctaccaagcc aggcaggtc                                               19


<210> SEQ ID NO 4
<211> LENGTH: 20
<212> TYPE: DNA
<213> ORGANISM: Artificial
<220> FEATURE:
<223> OTHER INFORMATION: Oligo nucleotide to act as a reverse primer for
      PCR.

<400> SEQUENCE: 4

gccattgtac ttgggcttgt                                              20
```